United States Patent
Rubio Martinez et al.

(10) Patent No.: US 10,301,331 B2
(45) Date of Patent: *May 28, 2019

(54) SEPARATION OF METAL-ORGANIC FRAMEWORKS

(71) Applicant: Commonwealth Scientific and Industrial Research Organisation, Acton, ACT (AU)

(72) Inventors: Marta Rubio Martinez, Clayton South (AU); Pablo Juliano, Clayton South (AU); Thomas Leong, Clayton South (AU); Matthew Roland Hill, Clayton South (AU); Kok Seng Lim, Clayton South (AU)

(73) Assignee: Commonwealth Scientific and Industrial Research Organisation (AU)

( * ) Notice: Subject to any disclaimer, the term of this patent is extended or adjusted under 35 U.S.C. 154(b) by 0 days.

This patent is subject to a terminal disclaimer.

(21) Appl. No.: 15/577,124

(22) PCT Filed: May 26, 2016

(86) PCT No.: PCT/AU2016/050410
§ 371 (c)(1),
(2) Date: Nov. 27, 2017

(87) PCT Pub. No.: WO2016/187669
PCT Pub. Date: Dec. 1, 2016

(65) Prior Publication Data
US 2018/0201629 A1    Jul. 19, 2018

(30) Foreign Application Priority Data
May 27, 2015   (AU) ................................ 2015901950

(51) Int. Cl.
*C07F 5/06* (2006.01)
*C07B 63/00* (2006.01)
(Continued)

(52) U.S. Cl.
CPC ............ *C07F 5/069* (2013.01); *B01D 21/283* (2013.01); *B01J 20/226* (2013.01);
(Continued)

(58) Field of Classification Search
None
See application file for complete search history.

(56) References Cited

U.S. PATENT DOCUMENTS 9,630,163 B2 *  4/2017  Rubio Martinez .. B01J 19/0006
10,010,860 B2 *  7/2018  Rubio Martinez .. B01J 19/0006
(Continued)

FOREIGN PATENT DOCUMENTS

WO    2004/112093 A2    12/2004
WO    2012/138419 A1    10/2012
(Continued)

OTHER PUBLICATIONS

International Search Report and Written Opinion for PCT/AU2016/050410 (dated Aug. 10, 2016).
(Continued)

*Primary Examiner* — Clinton A Brooks
(74) *Attorney, Agent, or Firm* — Merchant & Gould P.C.

(57) ABSTRACT

A method of separating a metal organic framework (MOF) from a solution and associated apparatus. The method comprises: providing a MOF containing solution; contacting the MOF containing solution with an acoustic reflector surface such that, any high frequency ultrasound applied within the MOF containing solution reflects off the acoustic reflector surface; and applying a high frequency ultrasound of at least 20 kHz to the MOF containing solution. The MOF material is substantially separated from solution as aggregated sediment that settles out of solution.

14 Claims, 13 Drawing Sheets

(51) Int. Cl.
  *B01J 20/22* (2006.01)
  *B01J 20/30* (2006.01)
  *B01J 20/28* (2006.01)
  *B01D 21/28* (2006.01)

(52) U.S. Cl.
  CPC ......... *B01J 20/28057* (2013.01); *B01J 20/30* (2013.01); *B01J 20/305* (2013.01); *C07B 63/00* (2013.01); *B01D 2253/204* (2013.01)

(56) References Cited

U.S. PATENT DOCUMENTS

| | | |
|---|---|---|
| 2013/0118958 A1 | 5/2013 | Farha et al. |
| 2016/0102284 A1 | 4/2016 | Lipkens et al. |

FOREIGN PATENT DOCUMENTS

| | | |
|---|---|---|
| WO | 2013/086585 A1 | 6/2013 |
| WO | 2014/013274 A2 | 1/2014 |

OTHER PUBLICATIONS

Australian Patent Office International-Type Search Report for Australian Patent Application No. 2015901950 (dated Sep. 25, 2015).
Bayliss et al., "Synthesis of Metal-Organic Frameworks by Continuous Flow", Green Chem., 16:1-16 (2014).
Gaab et al., "The progression of Al-based metal-oranic frameworks—From academic research to industrial production and applications", Microporous and Mesoporous Materials, 157:131-136 (2012).
Rubiio-Martinez et al., "Versatile, High Quality and Scalable Continuous Flow Production of Metal-Organic Frameworks", Scientific Reports, 4(5443):1-5 (2014).
International Preliminary Report on Patentability for PCT/AU2016/050410, 40 pp. (dated Sep. 22, 2017).
Extended European Search Report for European Patent Application No. 15892802.8 dated Jan. 11, 2019, 5 pages.
Haque, E. et al., "Facile Purification of Porous Metal Terephthalates with Ultrasonic Treatment in the Presence of Amides", Chemistry—A European Journal, 15(43): 11730-11736 (2009).

* cited by examiner (a)
Al-Fumarate supernatant (b)
MIL-53 (Al) supernatant

SEPARATION OF METAL-ORGANIC FRAMEWORKS

CROSS-REFERENCE

The present application is a U.S. National Stage Application under 35 U.S.C. § 371 of International Patent Application No. PCT/AU2016/050410 filed May 26, 2016, which claims the benefit of priority to Australian provisional patent application no. 2015901950 filed 27 May 2015, the disclosures of all of which are hereby incorporated by reference in their entireties. The International Application was published in English on Dec. 1, 2016 as WO 2016/187669.

TECHNICAL FIELD

The present invention generally relates to a method, system and apparatus for the separation for metal-organic frameworks (MOFs). The invention is particularly applicable for separation of MOFs from a MOF containing solution, as well as the separation of contaminants present in and around a MOF from the MOF and it will be convenient to hereinafter disclose the invention in relation to those exemplary applications. However, it is to be appreciated that the invention is not limited to that application and could be used in any MOF separation or purification step, process, system and/or apparatus.

BACKGROUND OF THE INVENTION

The following discussion of the background to the invention is intended to facilitate an understanding of the invention. However, it should be appreciated that the discussion is not an acknowledgement or admission that any of the material referred to was published, known or part of the common general knowledge as at the priority date of the application.

Metal-Organic Frameworks (MOFs) are a class of promising porous materials having tuneable functionality, large pore sizes and the highest known surface areas. These characteristics are of high interest for a myriad of industrial applications such as gas storage, gas separation, drug delivery and catalysis. However, to date the cost of these materials has remained prohibitively high, thereby restricting the ability of these materials to make a significant impact on prospective markets or technologies. Only seven MOFs out of the thousands of MOFS described in academic literature are commercially available, with that availability limited to small quantities (grams).

An important requirement for accessing the potential applications of MOFs is the ability to routinely synthesise MOF materials in large quantities (kg scale or higher) at an economic price point. Such a process needs to be a versatile, efficient and scalable synthesis that is able to produce MOFs in large quantities in order to introduce these materials to real world applications.

However, traditional laboratory routes such as the classical solvothermal synthesis are difficult to scale up due to the extended reaction times (~24 hours) and low quality material yield. Furthermore, a wide variety of available synthetic synthesis methods have a singular nature providing an inherent inflexibility for any prospective production process.

Large-scale process post synthesis steps such as cleaning, separation and activation can also be crucial for cost-effective production of high quality MOF material.

There are a number of known technologies for solid-liquid separation including centrifuges, cyclones, electrostatic precipitators, settling chambers, classifiers or filters, and evaporation. However, the small size of the MOF particles, their low concentration in the solvent, as well as their density approaching that of the solvent (due to the high porosity), makes separation unfeasible, inefficient or expensive at an industrial scale using most conventional methods.

Sedimentation- or tubular-type centrifuges are known to process solids as small as 100 nm, while wet electrostatic precipitators can also handle particles above 50 nm with 98% efficiency and greater than 100 nm with 95% efficiency. Yet, a high capital investment is generally required and this type of equipment also has generally high overall power consumption.

Liquid-solid filters can process particles as small as 500 nm, when operated under pressure (typically 2-15 bar for continuous rotary drum, or 3 to 70 bar for batch), or when using cartridge or sand (packed bed) filters (batch operation). However, filters requiring a high pressure drop across the separation stage are subject to fouling over time while pressurised rotary drum filters have a very high capital cost.

It would therefore be desirable to provide a new and/or improved method of separating and/or purifying a MOF in solution from contaminants, without destroying the integrity of the porous MOF.

SUMMARY OF THE INVENTION

The present invention provides a new separation apparatus, system and method that can separate and/or purify a metal organic framework content in a solution. The present invention also relates to a method, system and apparatus for washing and/or purification of metal-organic frameworks to remove contaminants, such as occluded unreacted ligands, from within pores of the metal organic framework in solution.

In a first aspect, the present invention provides a method of separating a metal organic framework (MOF) from a solution, comprising:

providing a MOF containing solution;

contacting the MOF containing solution with an acoustic reflector surface such that, any high frequency ultrasound applied within the MOF containing solution reflects off the acoustic reflector surface such that a standing wave is formed through constructive interference; and applying a high frequency ultrasound of at least 20 kHz, preferably between 20 kHz to 4 MHz, more preferably 500 kHz to 2 MHz, yet more preferably between 800 kHz and 2 MHz, and yet more preferably between 1 MHz and 2 MHz to the MOF containing solution;

thereby substantially separating the MOF from solution as an aggregated sediment which settles out of solution.

In some embodiments, a high frequency ultrasound of at least 400 kHz is used.

The present invention provides an ultrasonic and/or megasonic separation process, system and apparatus involving the application of high frequency ultrasound or megasonic frequencies to a MOF containing solution. Acoustic radiation from the applied ultrasonic (and in some embodiments megasonic) frequencies aggregate MOFs towards pressure nodes formed within the MOF-containing solution. The aggregated MOF material tends to sediment out of solution at a greatly accelerated rate to the bottom of a container or separation chamber housing the MOF containing solution. Ultrasonic and megasonic operation involves no moving parts, has a low surface area of contact with the fluid (i.e. lower capacity for fouling, ease of cleaning) and allows continuous separation, washing and/or purification of MOFs. Furthermore, the simplicity and speed of the process enables the process to be scaled, and applied economically to an existing MOF production method.

It should be appreciated that the separation or purification of the MOF according to the present invention occurs post-synthesis of the MOF in crude or pure form. Accordingly, the method of the present invention is used to separate MOF as an aggregated sediment in solid form, from a MOF containing solution once MOF synthesis is completed, or from a MOF containing solution in which the MOF has been added to that solution for a purpose or function or similar post MOF synthesis application.

It also should be appreciated that the MOF containing solution typically comprises a mixture or suspension of MOFs within the solution. In this regard, the MOF comprises a solid component or particles which are dispersed throughout the liquid of that solution. For ease of reference, this suspension of MOFs in solution will be referred to as a "MOF containing solution" in this specification. Typically, the MOF containing solution comprises MOFs which have unreacted ligands, metal salts or other contaminants trapped within the pores of the MOF.

The step of contacting the MOF containing solution with an acoustic reflector surface can comprise any arrangement in which the MOF containing solution is contacted or otherwise has a fluid connection with the reflector surface. In some embodiments, the step of contacting the MOF containing solution with an acoustic reflector surface comprises positioning or otherwise providing the acoustic reflector surface within the MOF containing solution. The acoustic reflector surface is preferably spaced away from the source of the high frequency ultrasound applied within the MOF containing solution that it reflects off the acoustic reflector surface such that a standing wave is formed through constructive interference. In this respect, the reflected sound waves are able to interact with the original transmitted wave. If the reflected and the transmitted wave are in phase, i.e. the peaks and troughs of the waves are aligned, then constructive interference will occur leading to resonance. With this occurrence, pressure nodes and anti-nodes will form along the path of the interacting sound waves at distances equal to multiples of half the wavelength of the waves.

The high frequency ultrasound can be applied or produced from any suitable device. In embodiments, the high frequency ultrasound is applied by high frequency transducer. The high frequency transducer and reflector surfaces are preferably parallel spaced apart within or relative to the MOF containing solution. Again, that spacing is suitable for the formation of a standing wave through constructive interference of the reflected and the transmitted wave (i.e. the reflected and the transmitted wave being in phase).

In some embodiments, the present invention provides a method of separating a metal organic framework (MOF) from a solution, comprising:

providing a MOF containing solution in a housing containing a high frequency transducer and an acoustic reflector surface, the transducer and the acoustic reflector surface being spaced apart within the housing such that a standing wave is formed through constructive interference; and operating the transducer to apply a high frequency ultrasound of at least 20 kHz to the MOF containing solution;

thereby substantially separating the MOF from solution as an aggregated sediment which settles out of the MOF containing solution, leaving any trapped ligands, metal salts or contaminants in solution.

The use of an acoustic reflector surface assists in the formation of a standing wave field required to form pressure nodes where particles are collected for cleaning or separation. Standing wave ultrasound fields are created by placing a reflecting surface in front of the transducer. The use of an acoustic reflector surface facilitates the formation of pressure nodes in the present invention.

The frequency of the applied high frequency ultrasound is important in the function and effect of the separation. Whilst the preferred frequency depends on factors such as MOF composition, particle size, solution composition and the like, the general ranges of applied high frequency ultrasound are as follows: In some embodiments, the applied high frequency ultrasound is between 20 kHz to 4 MHz, preferably 500 kHz to 2 MHz, more preferably between 800 kHz and 2 MHz, and yet more preferably between 1 MHz and 2 MHz. In some embodiments, the applied high frequency ultrasound is greater than 1 MHz, preferably between 1 MHz and 10 MHz, and more preferably between 1 and 4 MHz.

The formation of a standing wave depends on a variety of factors, including frequency, transducer and reflector spacing and the like. For example, in embodiments it would be possible that a standing wave field is formed with 100 kHz in larger vessels with node to node distance of 7.2 mm.

In some cases, it can be advantageous to move the applied high frequency ultrasound between a high frequency and a low frequency. In some embodiments, the applied high frequency ultrasound is cycled between a high frequency and a low frequency. Again, the selected frequencies depend on a number of factors. However, in some embodiments the high frequency is between 400 kHz to 2 MHz and the low frequency is between 20 kHz to 400 kHz. However, other embodiments the low frequency is between 20 kHz to 500 kHz and the high frequency is between 500 kHz to 2 MHz.

The energy density of the applied high frequency ultrasound is another factor which can affect separation. In some embodiments, the energy density of the applied high frequency ultrasound is at least 25 kJ/kg, preferably between 100 kJ/kg to 250 kJ/kg.

In some embodiments, the process and apparatus of the present invention has the ability to achieve specificity of separation based on particle size by tuning an operation parameter such as frequency and energy density. Thus, in some embodiments at least one of frequency or energy density of the applied high frequency ultrasound is tuned to selectively separate MOF and any contaminants in the MOF containing solution based on a specific particle size.

MOF material is extremely porous and therefore contaminant species in a solution during synthesis of a MOF can be trapped or otherwise located in the pores of the MOF material. Alternatively, the pores within a MOF could be contaminated or blocked during industrial application of MOFs. The process of the present invention can be used for separation and/or purification of MOFs from such contaminants, and more particularly contaminants in the pores of a MOF. Thus, in some embodiments, the MOF present in the MOF containing solution metal organic framework (MOF) includes at least one contaminant, and the method substantially separates the contaminant from the MOF within the solution. The contaminant is preferably left in solution and the MOF settles at or proximate the bottom of the solution as a solid sediment after treatment with high frequency ultrasound. Again, this separation process includes separation of contaminants in the pores of the MOF. The separation method of the present invention therefore provides an advantageous method of purifying a crude or contaminated MOF. The method according to the invention results in separation or purification of MOFs so that it is substantially free from unreacted metal salts, ligands or other contaminants within the pores of the MOF.

It should be appreciated that separation in this washing and purifying context broadly encompasses a number of unit processes including washing processes, purification processes, polishing processes and the like. All of these processes involve the separation of a product (in the present invention a MOF) from a contaminant or other material. It should be appreciated that all these process functions and similar processes are incorporated into the scope of the present invention.

The separation process of the present invention can comprise a washing procedure or process. In such embodiments, the step of providing the MOF containing solution preferably comprises adding a MOF to a washing solution. The washing solution can comprise any suitable solvent or dispersant. Suitable washing solutions include water, ethanol, dimethylformamide (DMF), methanol, tetrahydrofuran, chloroform, acetone, dichloromethane, ethyl acetate, diethylformamide or a combination thereof.

The MOF is preferably separated in greater purity from the washing solution following sedimentation at the bottom of the solution. The process therefore further comprises the step of isolating the MOF (from the solution which includes the MOF as an aggregated sediment). Isolation of the MOF can be achieved using any number of separation process steps including but not limited to decanting, filtration, evaporation, or centrifugation.

Following isolation, it may be preferable to wash or further treat the resultant MOF. The process of the present invention may therefore further comprise at least one additional washing step including the steps of:

isolating the MOF;

adding the isolated MOF to a washing solution;

contacting the MOF containing washing solution with an acoustic reflector surface such that, any high frequency ultrasound applied within the MOF containing washing solution reflects off the acoustic reflector surface such that a standing wave is formed through constructive interference; and applying a high frequency ultrasound of at least 20 kHz, preferably at least 400 kHz, preferably between 20 kHz to 4 MHz, preferably 500 kHz to 2 MHz, more preferably between 800 kHz and 2 MHz, and yet more preferably between 1 MHz and 2 MHz to a MOF containing solution, thereby separating the MOF, leaving any contaminants in the washing solution.

Again, the frequency of the applied high frequency ultrasound is important in the function and effect of the separation. Whilst the preferred frequency depends on factors such as MOF composition, particle size, solution composition and the like, the general ranges of applied high frequency ultrasound are as follows: In some embodiments, the applied high frequency ultrasound is between 20 kHz to 4 MHz, preferably 500 kHz to 2 MHz, more preferably between 800 kHz and 2 MHz, and yet more preferably between 1 MHz and 2 MHz.

In some embodiments, a plurality of washing steps outlined above is used.

In some embodiments, the present invention can be used to separate small MOF particles from the mother liquid produced after production of a MOF. In such embodiments, the MOF containing solution comprises a mother liquid from a MOF forming process. Furthermore, at least one contaminant can include occluded unreacted ligands within pores of the MOF.

The present invention can also be used to improve the surface area of the final product, providing an advantageous alternative to time consuming and costly calcinations traditionally used for surface area improvement of MOFs. The process can therefore assist in maintaining MOF product quality i.e. porosity, thermal and chemical stability. Thus, in some embodiment the method also improves the BET surface area of the MOF, preferably by at least 20%, preferably 30% compared to a centrifuge washed MOF.

The MOF containing solution comprises a MOF material in a solution. The solution can comprise any suitable solvent or dispersant including water, ethanol, dimethylformamide (DMF), methanol, acetone, tetrahydrofuran, chloroform, dichloromethane, ethyl acetate, diethylformamide or a combination thereof. Preferably, the MOF containing solution is used at ambient or room temperature.

A large variety of MOFs or MOF materials can be used with the present invention.

It should be appreciated that Metal Organic Frameworks (MOFs) (also known as coordination polymers) or MOFs are class of hybrid crystal materials where metal ions or small inorganic nano-clusters are linked into one-, two- or three-dimensional networks by multi-functional organic linkers. In this sense, a MOF is a coordination network with organic ligands containing potential voids or pores. A coordination network is a coordination compound extending, through repeating coordination entities, in one dimension, but with cross-links between two or more individual chains, loops, or spiro-links, or a coordination compound extending through repeating coordination entities in two or three dimensions and finally a coordination polymer is a coordination compound with repeating coordination entities extending in one, two, or three dimensions.

MOFs have many appealing features having surface areas of thousands of square meters per gram, extremely low density, interconnected cavities and very narrow porosity distributions. A variety of open micro- and mesoporous structures can be developed, leading to materials with extreme surface area.

Examples of metal organic frameworks which may be suitable for use in the present invention include those commonly known in the art as MOF-177, MOF-5, IRMOF-1, IRMOF-8, Al-fum (Aluminium fumarate), Zr-fum (Zirconium fumarate), UiO-66, HKUST-1, NOTT-400, MOF-74 and MIL-53 (aluminium terephthalate). It should be appreciated that the present invention is suitable for use with a large number of MOFs and should therefore not be limited to the exemplified MOF structures in the present application.

MOFs used in the process of the present invention preferably comprise a plurality of metal clusters, each metal cluster including one or more metal ions; and a plurality of charged multidentate linking ligands connecting adjacent metal clusters. Such MOFs can therefore be more generally defined by the charged multidentate linking ligands connecting adjacent metal clusters which are used to form each MOF.

Each metal cluster preferably includes one or more metal ions. As used herein, the term "cluster" means a moiety containing one or more atoms or ions of one or more metals or metalloids. This definition embraces single atoms or ions and groups of atoms or ions that optionally include ligands or covalently bonded groups. Each cluster preferably comprises two or more metal or metalloid ions (hereinafter jointly referred to as "metal ions") and each ligand of the plurality of multidentate ligand includes two or more carboxylates.

Typically, the metal ion is selected from the group consisting of Group 1 through 16 metals of the IUPAC Periodic Table of the Elements including actinides, and lanthanides, and combinations thereof. Preferably, the metal ion is selected from the group consisting of $Li^+$, $Na^+$, $K^+$, $Rb^+$, $Be^{2+}$, $Mg^{2+}$, $Ca^{2+}$, $Sr^{2+}$, $Ba^{2+}$, $Sc^{3+}$, $Y^{3+}$, $Ti^{4+}$, $Zr^{4+}$, $Hf^{4+}$, $V^{4+}$, $V^{3+}$, $V^{2+}$, $Nb^{3+}$, $Ta^{3+}$, $Cr^{3+}$, $Mo^{3+}$, $W^{3+}$, $Mn^{3+}$, $Mn^{2+}$, $Re^{3+}$, $Re^{2+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Rh^{2+}$, $Rh^+$, $Ir^{2+}$, $Ir^+$, $Ni^{2+}$, $Ni^+$, $Pd^{2+}$, $Pd^+$, $Pt^{2+}$, $Pt^+$, $Cu^{2+}$, $Cu^+$, $Ag^+$, $Au^+$, $Zn^{2+}$, $Cd^{2+}$, $Hg^{2+}$, $B^{3+}$, $B^{5+}$, $Al^{3+}$, $Ga^{3+}$, $In^{3+}$, $Tl^{3+}$, $Si^{4+}$, $Si^{2+}$, $Ge^{4+}$, $Ge^{2+}$, $Sn^{4+}$, $Sn^{2+}$, $Pb^{4+}$, $Pb^{2+}$, $As^{5+}$, $As^{3+}$, $As^+$, $Sb^{5+}$, $Sb^{3+}$, $Sb^+$, $Bi^{5+}$, $Bi^{3+}$, $Bi^+$, and combinations thereof.

Typically, the cluster has formula $M_mX_n$ where M is the metal ion, X is selected from the group consisting of Group 14 through Group 17 anion, m is an number from 1 to 10, and n is a number selected to charge balance the cluster so that the cluster has a predetermined electric charge Preferably, X is selected from the group consisting of $O^{2-}$, $N^{3-}$ and $S^{2-}$. Preferably. M is selected from the group consisting of $Li^+$, $K^+$, $Na^+$, $Cs^+$, $Mg^{2+}$, $Ca^{2+}$, $Sr^{2+}$, $Ba^{2+}$, $V^{2+}$, $V^{3+}$, $V^{4+}$, $V^{5+}$, $Mn^{2+}$, $Re^{2+}$, $Fe^{2+}$, $Fe^{3+}$, $Ru^{3+}$, $Ru^{2+}$, $Os^{2+}$, $Co^{2+}$, $Rh^{2+}$, $Ir^{2+}$, $Ni^{2+}$, $Pd^{2+}$, $Pt^{2+}$, $Cu^{2+}$, $Zn^{2+}$, $Cd^{2+}$, $Hg^{2+}$, $Si^{2+}$, $Ge^{2+}$, $Sn^{2+}$, and $Pb^{2+}$. More preferably M is $Zn^{2+}$ and X is $O^{2-}$.

Typically, the multidentate linking ligand has 6 or more atoms that are incorporated in aromatic rings or non-aromatic rings. Preferably, the multidentate linking ligand has 12 or more atoms that are incorporated in aromatic rings or non-aromatic rings. More preferably, the one or more multidentate linking ligands comprise a ligand selected from the group consisting of ligands having formulae 1 through 27:

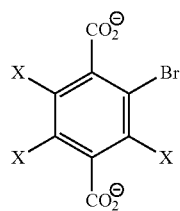

1

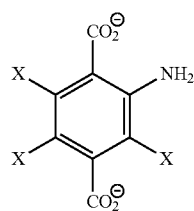

2

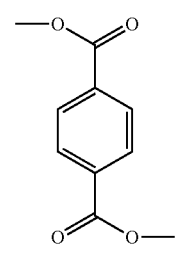

3

-continued

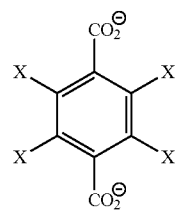

4

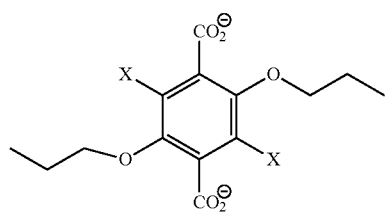

5

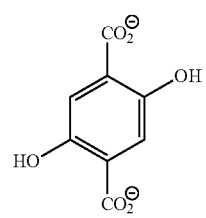

6

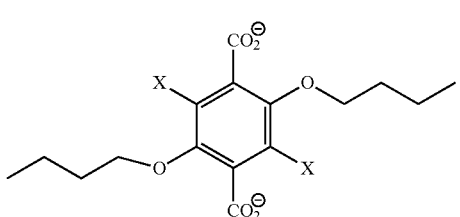

7

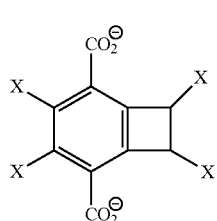

8

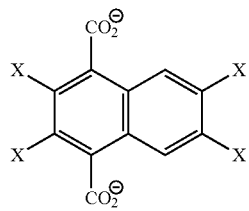

9

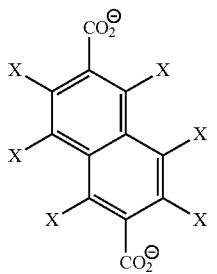

10

11
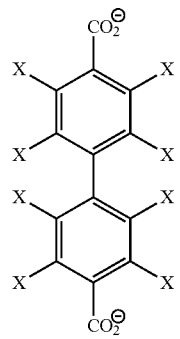
12
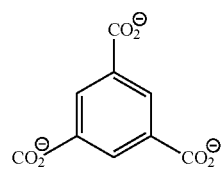
13
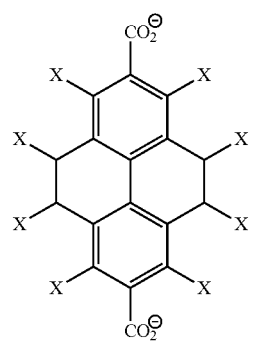
14
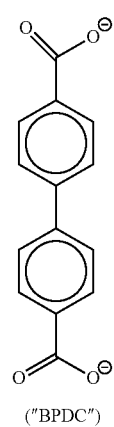
("BPDC")
15
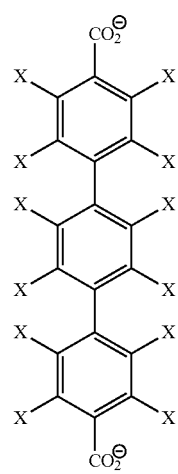
16
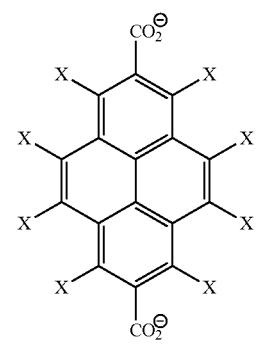
17
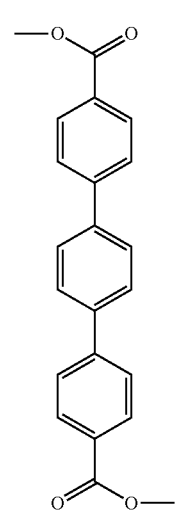

-continued
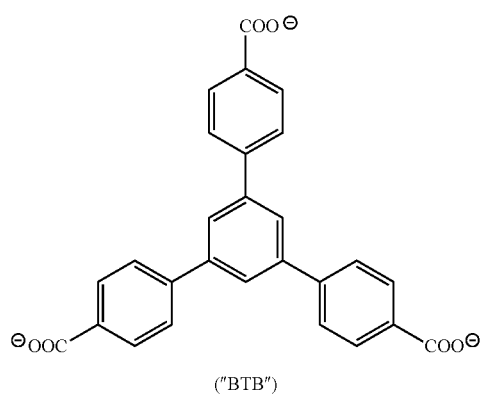
("BTB")
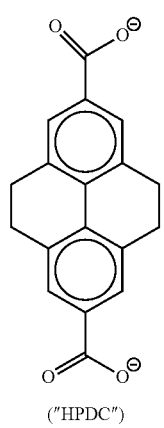
("HPDC")
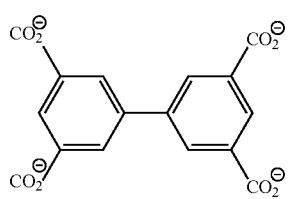
(BPTC)
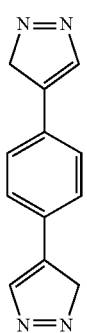
-continued
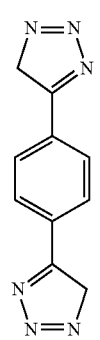
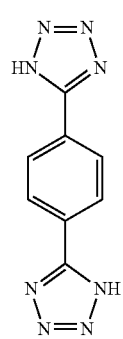
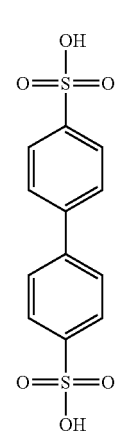
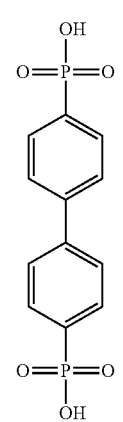

-continued

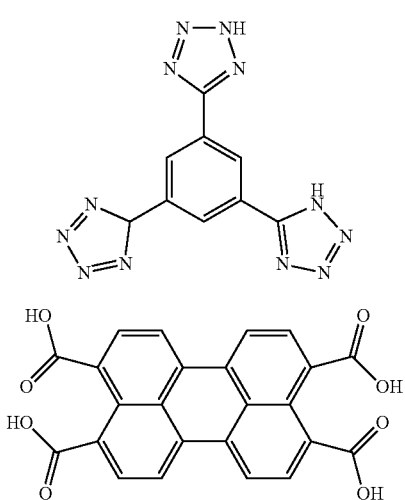

wherein X is hydrogen, —NHR, —N(R)$_2$, halides, C$_{1-10}$ alkyl, C$_{6-18}$ aryl, or C$_{6-18}$ aralkyl, —NH$_2$, alkenyl, alkynyl, —Oalkyl, —NH(aryl), cycloalkyl, cycloalkenyl,cycloalkynyl, —(CO)R, —(SO$_2$)R, —(CO$_2$)R—, —SH, —S(alkyl), —SO$_3$H, —SO$_3$_M$^+$, —COOH, —COO$^-$M$^+$, —PO$_3$H$_2^-$, —PO$_3$H$^-$M$^+$, —PO$_3^{2-}$M$^{2+}$, or —PO$_3^{2-}$M$^{2+}$, —NO$_2$, —CO$_2$H, silyl derivatives; borane derivatives; and ferrocenes and other metallocenes; M is a metal atom, and R is C$_{1-10}$ alkyl.

In one embodiment, the multidentate linking ligand comprises a ligand having formula 3 previously described. In another embodiment, the multidentate linking ligand comprises a ligand having formula 18 ("BTB"). In a further embodiment, the multidentate linking ligand comprises a ligand having formula 14.

A second aspect of the present invention provides an apparatus for separating a metal organic framework (MOF) from a MOF containing solution, comprising:

a housing having a reservoir capable of receiving a MOF containing solution;

a high frequency ultrasound transducer operatively connected to the reservoir and capable of applying frequencies of at least 20 kHz, preferably between 20 kHz to 4 MHz, more preferably 500 kHz to 2 MHz, more preferably between 800 kHz and 2 MHz, and yet more preferably between 1 MHz and 2 MHz to the MOF containing solution; and an acoustic reflector surface spaced apart from the transducer within the housing, the transducer, in use, being operated to reflect said applied high frequency ultrasound off the acoustic reflector surface, said acoustic reflector surface being spaced away from the high frequency ultrasound transducer such that a standing wave is formed through constructive interface.

The apparatus of this second aspect of the present invention comprises a separation apparatus for metal-organic frameworks. In use, a high frequency ultrasound is applied to the MOF containing solution to effect separation of the MOF from the solution. The apparatus can also be used for a washing or purification method. The MOF includes at least one contaminant and the apparatus is used to separate those one or more contaminants from the MOF.

Once again, the frequency of the applied high frequency ultrasound is important in the function and effect of the separation. Whilst the preferred frequency depends on factors such as MOF composition, particle size, solution composition and the like, the general ranges of applied high frequency ultrasound the transducer is capable of applying to a MOF containing solution are as follows: In some embodiments, the applied high frequency ultrasound is between 20 kHz to 4 MHz, preferably 500 kHz to 2 MHz, more preferably between 800 kHz and 2 MHz, and yet more preferably between 1 MHz and 2 MHz. In some embodiments, the applied high frequency ultrasound is greater than 1 MHz, preferably between 1 MHz and 10 MHz, and more preferably between 1 and 4 MHz.

The Applicant considers that the size, material and/or geometry of the reactor vessel may have an effect on the outcome (degree, efficiency or the like) of ultrasonic and/or megasonic separation process of MOFs. Similarly, the positioning, arrangement and alignment of transducers within a separation apparatus may have an effect on the outcome (degree, efficiency or the like) of megasonic separation process of MOF.

The transducer can be positioned in any suitable location in relation to the housing to apply the megasonic frequencies to the MOF containing liquid received within the reservoir. In some embodiments, the housing comprises a container including at least one wall position to contact the MOF containing solution, and the transducer is high frequency ultrasound transducer is position within the reservoir or in engagement with the at least one wall. In each case, the transducer is operable to apply ultrasonic and/or megasonic frequencies to a MOF containing solution housed in the reservoir.

The transducer can comprise any suitable high frequency ultrasound transducer. In some embodiments, the high frequency ultrasound transducer comprises a plate transducer.

The acoustic reflection of the applied frequencies assists the MOF separation process. Accordingly, in some embodiments the housing includes at least one reflector surface designed to reflect the applied megasonic frequencies within the reservoir. The transducer is operated to apply a high frequency ultrasound to the MOF containing solution and to reflect said applied ultrasound from the acoustic reflector surface. The use of an acoustic reflector surface assists in the formation of a standing wave field required to form pressure nodes where particles are collected for cleaning or separation. This substantially separates the MOF from solution as an aggregated sediment which settles out of solution.

The acoustic reflector surface is generally located in front of the transducer, and spaced apart from that transducer. In some embodiments, the transducer is located proximate or at one wall or side of the housing, and the acoustic reflector surface is located proximate or at an opposite wall or side of the housing.

It should be appreciated that the apparatus of this second aspect can include all of the features discussed above in relation to the first aspect of the present invention. Similarly, the method of the first aspect of the present invention can utilise an apparatus of the second aspect of the present invention therein.

A third aspect of the present invention provides a process of producing a metal organic framework (MOF), comprising:

forming a MOF in a reactor; and isolating, washing and/or purifying the MOF using an apparatus according to the second aspect of the present invention.

A fourth aspect of the present invention provides a system for producing a metal organic framework (MOF), comprising:

a reactor for forming a MOF from precursor materials; and an apparatus for washing and/or purifying the MOF according to the second aspect of the present invention.

Any suitable reactor can be used in the third and fourth aspects of the present invention. In some embodiments, the reactor is a batch reactor, for example a stirred reactor. In other embodiments, the reactor is a continuous flow reactor. In preferred embodiments, the reactor comprises a coiled continuous flow reactor. It should be appreciated that the MOF can be treated in the apparatus according to the second aspect of the present invention and can either be provided in solution, for example a mother liquid produced from the reactor, or be introduced/added into a solvent or liquid dispersant such as water, ethanol, methanol, DMF or the like to form a MOF containing solution suitable for use in said apparatus.

A fifth aspect of the present invention provides a method of separating a metal organic framework (MOF) from at least one contaminant, comprising:

providing a MOF containing solution which includes a MOF and at least one contaminant;

contacting the MOF containing solution with an acoustic reflector surface such that, any high frequency ultrasound applied within the MOF containing solution reflects off the acoustic reflector surface such that a standing wave is formed through constructive interference; and applying a high frequency ultrasound of at least 20 kHz, at least 400 kHz, preferably between 20 kHz to 4 MHz, more preferably 500 kHz to 2 MHz, yet more preferably between 800 kHz and 2 MHz, and yet more preferably between 1 MHz and 2 MHz to the MOF containing solution, thereby substantially separating the contaminant from the MOF.

A sixth aspect of the present invention provides a method of activation of a metal organic framework (MOF), comprising:

providing a MOF containing solution;

contacting the MOF containing solution with an acoustic reflector surface such that, any high frequency ultrasound applied within the MOF containing solution reflects off the acoustic reflector surface such that a standing wave is formed through constructive interference; and applying a high frequency ultrasound of at least 20 kHz, preferably at least 400 kHz, preferably between 20 kHz to 4 MHz, more preferably 500 kHz to 2 MHz, yet more preferably between 800 kHz and 2 MHz, and yet more preferably between 1 MHz and 2 MHz to the MOF containing solution, thereby improving the surface area and activation properties of the MOF.

A seventh aspect of the present invention provides a method of improving the surface area of a metal organic framework (MOF), comprising:

providing a MOF containing solution;

contacting the MOF containing solution with an acoustic reflector surface such that, any high frequency ultrasound applied within the MOF containing solution reflects off the acoustic reflector surface; and applying a high frequency ultrasound of at least 20 kHz, preferably at least 400 kHz, preferably between 20 kHz to 4 MHz, more preferably 500 kHz to 2 MHz, yet more preferably between 800 kHz and 2 MHz, and yet more preferably between 1 MHz and 2 MHz to the MOF containing solution, thereby improving the surface area of the MOF.

Again, for each of the fifth, sixth and seventh aspects of the present invention, an acoustic reflector surface can be used to assist the formation of pressure nodes with the MOF containing solutions. In such embodiments, the method further includes the step of:

contacting the MOF containing solution with an acoustic reflector surface such that, any high frequency ultrasound applied within the MOF containing solution reflects off the acoustic reflector surface.

Again, this step of contacting the MOF containing solution with an acoustic reflector surface can comprise any arrangement in which the MOF containing solution is contacted or otherwise has a fluid connection with the reflector surface. In some embodiments, the step of contacting the MOF containing solution with an acoustic reflector surface comprises positioning or otherwise providing the acoustic reflector surface within the MOF containing solution. The acoustic reflector surface is preferably spaced away from the source of the high frequency ultrasound applied within the MOF containing solution that it reflects off the acoustic reflector surface such that a standing wave is formed through constructive interference. In this respect, the reflected sound waves are able to interact with the original transmitted wave. If the reflected and the transmitted wave are in phase, i.e. the peaks and troughs of the waves are aligned, then constructive interference will occur leading to resonance. With this occurrence, pressure nodes and anti-nodes will form along the path of the interacting sound waves at distances equal to multiples of half the wavelength of the waves.

In these and other embodiments of the present invention, the MOF containing solution is preferably provided into a housing containing a high frequency transducer and an acoustic reflector surface, the transducer and the acoustic reflector surface being spaced apart within the housing; and the transducer is operated to apply a high frequency ultrasound of at least 20 kHz, preferably between 20 kHz to 4 MHz, preferably 500 kHz to 2 MHz, more preferably between 800 kHz and 2 MHz, and yet more preferably between 1 MHz and 2 MHz to the MOF containing solution thereby substantially separating the MOF from solution as an aggregated sediment which settles out of solution. The use of an acoustic reflector surface assists in the formation of a standing wave field required to form pressure nodes where particles are collected for cleaning or separation.

The BET surface area of the MOF is preferably improved at least 20%, and more preferably 30% compared to a centrifuge washed MOF as it removes unreacted reagents trapped within the pores of the MOF.

Activation of a MOF using this aspect of the present invention is an important step for cost-effective and green production of MOFs as similar surface areas have only been obtained using laboratory scale methods that would be expensive at large scale, namely by using supercritical ethanol or calcination up to 330° C.

It should be appreciated that the apparatus of this fifth, sixth and seventh aspect can include all of the features discussed above in relation to the first and second aspects of the present invention.

BRIEF DESCRIPTION OF THE DRAWINGS

The present invention will now be described with reference to the figures of the accompanying drawings, which illustrate particular preferred embodiments of the present invention, wherein.

DETAILED DESCRIPTION

Figure 1A:
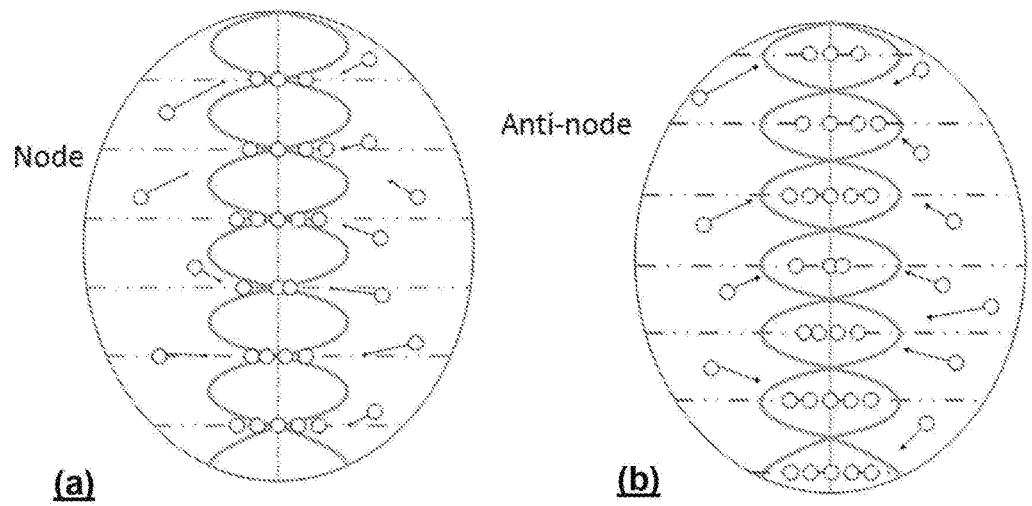
FIG. 1A illustrates the nodal planes of acoustic resonant wave of (a) node and (b) antinode sections of a wave. Particle agglomeration occurs at either the nodes or antinodes of the wave.

The present invention provides a new separation apparatus, system and method that can separate a metal-organic framework (MOF) from a solution. The method has also been found to purify the MOF, removing contaminants from the pores of the MOF and also improve the surface area of the treated MOF, producing a purified MOF having a higher surface area than comparable commercially available samples.

In this regard, the Inventors have surprisingly found that the use of ultrasonic and/or megasonic frequencies not only separates MOF material/particles from other components in a solution, but also purifies and activates the separated MOF. A MOF is extremely porous and therefore contaminant species in a solution can be trapped or otherwise located in these pores. The method, system and apparatus of the present invention have been found to substantially remove any contaminants from the pores of MOF material treated with the megasonic method and apparatus. This produces a desirable substantially pure MOFs which is highly scalable.

Furthermore, the Inventors have also surprisingly found that the use of ultrasonic, preferably megasonic frequencies also improves the surface area of the final product, acting as an alternate process to the time consuming and costly calcinations traditionally used for surface area improvement. The process can therefore assist in maintaining MOF product quality i.e. porosity, thermal and chemical stability.

The present invention can therefore permit large-scale production of MOFs at drastically reduced costs, allowing commercialisation of these MOFs for many potential real world applications. The present invention provides a fast, cost-effective, lowered environmental impact strategy to produce high-quality MOFs at a large scale.

The present invention uses megasonics technology for separation and activation of metal organic frameworks. The Inventors believe that this is the first time that ultrasonic frequencies and more particularly megasonic frequencies have been used for the separation of MOFs. Furthermore, the Inventors believe that this is the first time that megasonics has been used for the purification/activation of porous materials, and in particular MOFs.

Separation according to the present invention applies >20 kHz, in some cases >400 kHz, preferably between 20 kHz to 4 MHz, preferably 500 kHz to 2 MHz, more preferably between 800 kHz and 2 MHz, and yet more preferably between 1 MHz and 2 MHz high frequency ultrasound to create a standing wave, i.e. regions of minimal pressure (nodes) and maximal pressure (antinodes) within a liquid filled separation chamber. Whilst not wishing to be limited to any one theory, the Inventor's consider that when using this method, suspended particles or droplets migrate specifically towards one of these two regions due to acoustic radiation forces, based on their density and compressibility. In general, the aggregated MOFs are slightly denser than the surrounding fluid, and migrate towards the pressure nodes. This gathering of MOF material enhances the tendency to form larger aggregates which then sediment at a greatly accelerated rate to the bottom of the separation chamber, where they can be collected.

The process and apparatus of the present invention also has the ability to achieve specificity of separation based on particle size by tuning of the operation parameters such as frequency and energy density.

Furthermore, the application of the sound waves dramatically enhances the rate of separation, and hence reduces the chemical requirement and environmental footprint of conventional separation processes such as flocculation and sedimentation. This can be seen in a comparison of cleaning and separation techniques shown in Table 1:

TABLE 1

Comparison of cleaning and separation techniques using MIL-53 as a control

| Methods | MOF Separation | Activation time | Temperature (° C.) | SA$_{BET}$ (m²/g) |
|---|---|---|---|---|
| Centrifuge[1] | Yes | 1 min | Room Temp | 806 |
| Megasonics[1] | Yes | 10 min | Room Temp | 1183 |
| Ultrasound in the presence of Amides[2] | No | 40 min | 70 | 787 |
| Ultrasound in the presence of Amides[2] | No | 1 hour | 70 | 1425 |
| Supercritics[3] | Yes | 4 hours | 250° C. and 100 bar | 1010 |
| Calcination[2] | No | 72 hours | 325 | 1256 |

[1]Applicant's experiments.
[2]M. Gaab, N. Trukhan, S. Maurer, R. Gummaraju and U. Müller, *Microporous Mesoporous Mater.*, 2012, 157, 131-136.
[3]P. A. Bayliss, I. A. Ibarra, E. Pérez, S. Yang, C. C. Tang, M. Poliakoff and M. Schröder, *Green Chem.*, 2014, 16, 3796.

Ultrasonics and/or megasonic operation involves no moving parts, and can have a low surface area of contact with the fluid providing a lower capacity for fouling, and ease of cleaning. A separator according to the present invention essentially comprises a housing or container in which a liquid reservoir can be formed. The liquid reservoir is filled with a MOF containing solution. A high frequency transducer, such as a plate transducer is either submerged in the liquid filled reservoir or engaged with a wall of reservoir to project megasonic frequencies through the MOF containing solution for a certain length of time to effects the desired separation of MOF from solution and/or separation of contaminants from the MOF into the solution.

The Applicant considers that the size, material and/or geometry of the reactor vessel may have an effect on the outcome (degree, efficiency or the like) of the separation process of MOFs using the present invention. Similarly, the positioning, arrangement and alignment of transducers within a separation apparatus may have an effect on the outcome (degree, efficiency or the like) of the separation process of MOFs.

The Applicant notes that ultrasonics and megasonics are a well know separation technique for particles, particularly in the biotechnology and food processing areas. Previous applications of ultrasonics and megasonic involved liquid/liquid and solid/liquid separation especially in food processing (milk fat separation and palm oil separation). However, the Inventors are not aware of any previous published work using ultrasound, in particular megasonics, for the combined separation, washing, and/or activation of any porous material.

The inventors believe that the ultrasonic and megasonic ranges of the present invention provide at least one of surface area improvement, separation and/or washing properties for MOF containing solutions. The difference between ultrasonic and megasonics lies in the frequency that is used to generate the acoustic waves. Ultrasonic uses lower frequencies (20 kHz to 400 kHz) and produces random cavitations. Megasonic uses higher frequencies frequency (>0.4 MHz to several MHz) and produces controlled and smaller cavitations which allows the separation of nanocrystals (in our case, the MOFs). Furthermore, higher megasonic frequencies do not cause the violent cavitation effects found with ultrasonic frequencies. This significantly reduces or eliminates cavitation erosion and the likelihood of surface damage to the product being cleaned.

Again, it should be appreciated that the MOF containing solution typically comprises a mixture or suspension of the MOF particles within the solution. In this regard, the MOF comprises a solid component or particles which are dispersed throughout the liquid of that solution. For ease of reference, this suspension of MOF particles in solution will be referred to as a MOF containing solution in this specification.

The separation method and apparatus of the present invention utilises a reflector within the separation arrangement. Without wishing to be limited to any one theory, the Inventors have found that introducing a reflector allows a standing wave to be formed through constructive interference. As the soundwaves from the transducer reach the reflector, they are reflected where they may interact with the original transmitted wave. If the reflected and the transmitted wave are in phase, i.e. the peaks and troughs of the waves are aligned, then constructive interference will occur leading to resonance. With this occurrence, pressure nodes and anti-nodes will form along the path of the interacting sound waves at distances equal to multiples of half the wavelength of the waves.

Particles in the vicinity of these nodes and anti-nodes experience a series of forces as a result of the sounds resonance, these are known as the primary acoustic radiation force and the Bejerknes force (or secondary acoustic radiation force). These forces will cause the solid MOF species to agglomerate at the nodes or anti-nodes, increasing the rate of settling (given their density is greater than the fluid). After time, the solids will deposit within a bed forming solids lean supernatant.

Acoustic cavitation within a liquid is a possibility when operating with megasonics; the intense pressure of the ultrasonic waves has the capability to cause dissolved gases to exit solution leading to the formation of bubbles. Upon collapsing, extreme temperatures and pressures can be achieved of up to 10,000 K and many hundreds of bar respectively.

Increasing the ultrasounds frequency has the effect of smaller bubbles as they collapse faster under the more intense conditions. These smaller bubbles collapse with less energy, leading to less cavitation. The range of ultrasonic frequencies over which cavitation can be observed is typically between 20 kHz to 4 MHz.

The primary acoustic radiation force ($F_{ac}$) is a second order, non-linear force that acts upon particles within an acoustic standing wave field. Momentum is transferred from the soundwave to the solid, allowing its manipulation in the direction parallel to the soundwaves propagation. For an ideal standing wave, the time averaged force in the direction of the sounds propagation can be described by:

$$F_{ac} = -\frac{4\pi}{3} R^3 k E_{ac} \phi \sin(2kx) \quad [2.1]$$

$$k = \frac{2\pi}{\lambda} \quad [2.2]$$

$$\delta = \frac{5\rho_p - 2\rho_m}{2\rho_p + \rho_m} - \frac{\beta_p}{\beta_m} \quad [2.3]$$

Where:
R Is the Particle Radius
k is the wavenumber
$E_{ac}$ is the specific energy density
φ is the acoustic contrast factor $\rho_m$, $\rho_p$ is the density of the medium or particle respectively $\beta_m$, $\beta_p$ is the compressibility of the medium or particle respectively The compressibility of the particle can be estimated from the following relation:

$$\beta_p = \frac{1}{\rho_p c^2} \quad [2.4]$$

The acoustic contrast factor determines whether the solids will be driven to the nodal or anti-nodal planes of the resonance field. A negative factor (<0) indicates the particles will be displaced to the pressure anti-nodes within the field, whilst a positive factor (>0) indicates the particles will be displaced to the pressure node planes (see FIG. 1A). An acoustic contrast factor of 0 means separation cannot be obtained within the fluid medium via primary radiation forces. Typically particles have densities higher, and compressibility's lower than the surrounding fluid and will move to the pressure anti-node of the system.

Figure 1B:
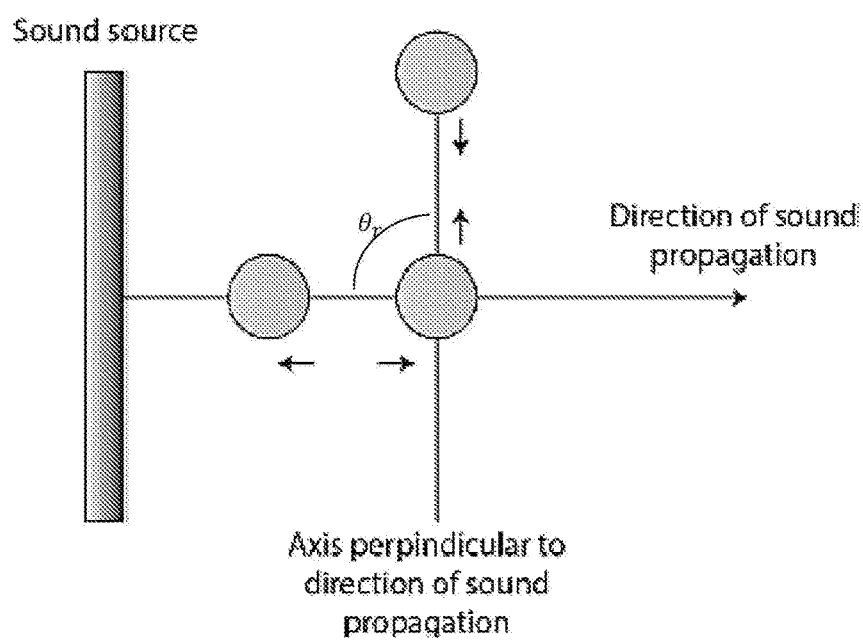
FIG. 1B illustrates the direction of secondary acoustic radiation force on two particles.

The secondary acoustic radiation force ($F_{sec}$), also known as the Bejerknes force acts upon the particles within the nodal plane pushing them towards each other and resulting in aggregation. Outside of the nodal planes, at angles other than 90°, the particles are repulsed as shown in FIG. 1B. The force can be described by the following:

$$F_{sec} = 4\pi R_{p_1}^3 R_{p_2}^3 \left( \frac{(3\cos^2\theta_r - 1)(\rho_p - \rho_m)^2 v^2}{6\rho_m d^4} - \frac{(\beta_p - \beta_m)^2 \rho_m \omega^2 p^2}{9d^2} \right) \quad [2.5]$$

Where:
$R_{p_1}$, $R_{p_2}$ is the radius of the two interacting particles
$\theta_r$ is the angle of the connection between the two particles, relative to the direction of sound propagation
p is the acoustic pressure
v is the velocity of the wave in a 1-D acoustic plane
d is the centre to centre distance between the particles
$\omega$ is the angular frequency of the oscillation The force results from the scattering of the sound waves from neighbouring particles within a sound field.

Figure 1C:
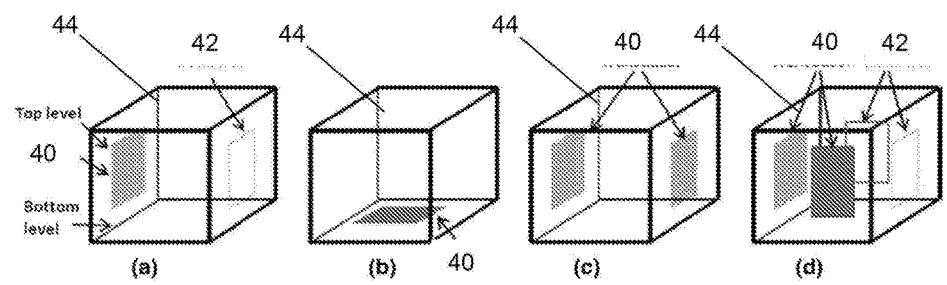
FIG. 1C illustrates various alignments of transducers within a housing for use in the method and apparatus of the present invention, namely a) Single transducer with vertical alignment, b) single transducer with horizontal alignment, c) dual transducers with vertical and parallel alignment, d) dual transducers with vertical and perpendicular alignment.
Figure 1D:
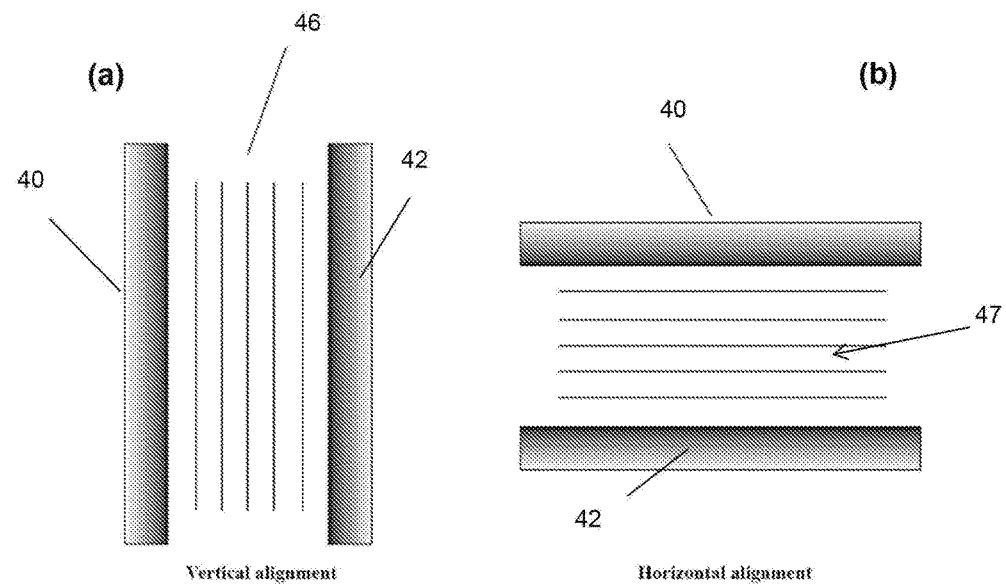
FIG. 1D illustrates (a) vertical and (b) horizontal alignment of the transducer and/or reflector for megasonic separation.

Transducer alignment needs to be considered in the positioning of the transducer 40 and reflector 42 within a housing 44 of a separation apparatus according to the present invention to generate standing waves. A vertical or horizontal alignment between the transducer 40 and reflector 42 refers to whether the transducer 40 or reflector 42 is positioned in a way that the nodal/antinodal bands are aligned in the vertical or horizontal plane (see FIGS. 1C and 1D).

Where gravity is a necessary mechanism for enhanced separation (i.e., product collects at the top or bottom of the container), a vertical alignment (see FIG. 1D(a)) is more amenable to separation since once product is aggregated to a sufficient size, the product can sediment or rise rapidly due to buoyancy. Vertical alignment bands 46 are formed when applying ultrasound in pulses.

A horizontal alignment (see FIG. 1D(b)), however, hinders this natural rise/fall since the product must pass through aligned bands that can "trap" the aggregated material prior to eventual rising/falling beyond the active processing region. Applying ultrasound in pulses can intermittently release product trapped in the horizontally aligned bands 47, but decreases the energy input to the system per unit time.

The Inventors have found that both types of alignments can be successfully applied for use of MOFs activation and separation. However, due to the above outlined reasons, the horizontal alignment requires additional time for settling the MOF crystals at the bottom of the vessel.

Sound wave attenuation may also be a factor to consider during the separation process. As the wave propagates through the medium, its energy will dissipate into mainly the form of heat. The rate at which this attenuation occurs depends upon the medium (both the fluid and the suspended solid) which the sound is travelling through in addition to frequency. Higher frequencies experience more rapid attenuation in a media; hence lower frequencies may be favoured with care taken to avoid cavitation.

In achieving separation, care must be taken to ensure the distance over which the sound must travel (to reflector and back) is not such that excessive attenuation occurs, resulting in weak acoustic separation forces. Whilst the volume which can be separated may increase with a larger separation distance between transducer and reflector, the rate of separation may be adversely affected in doing so. Sound wave attenuation is proportional to frequency, such that increasing the frequency will reduce the distance over which the separation will be effective.

Particle size may also have significant effect upon the separation process given both the primary and secondary acoustic radiation forces are proportional to the cubed radius (Eqn. 2.1 and 2.5). Therefore a larger particle is more easily manipulated than a smaller particle; however particles that are too large could interrupt the standing field of the resonance wave.

Acoustic streaming occurs when the fluid bulk is set in motion due to the sound wave oscillations which can overcome the manipulative acoustic radiation forces acting on the nodal and anti-nodal separation planes.

Acoustic attenuation, amongst other mechanisms, tends to lead to the occurrence of acoustic streaming. Attenuation scales with square of the frequency of the sound wave, as described by:

$$\alpha = \frac{2\mu(2\pi f)^2}{3\rho_m c^3} \quad [2.6]$$

Where:
$\mu$ is the viscosity
$\rho_m$ is the density of the medium

Hence increasing the frequency and amplitude of the sound wave will result in more significant streaming which may severely hinder the separation process.

EXAMPLES

The separation of two studied MOFs, aluminium fumarate (Al-fum) and aluminium terephthalate (MIL-53) using a Megasonic separation process and apparatus according the present invention, will now be exemplified by example. However, it should be appreciated that the present invention is suitable for use with a large number of MOFs and should therefore not be limited to the exemplified MOF structures in these examples. The examples provided can therefore be more generally applied to a wide range of MOFs.

Example 1

MOF Separation

MOF Synthesis

Aluminium fumarate (Al-fum) and aluminium terephthalate (MIL-53) were synthesized using flow chemistry technology following the methodology taught in Rubio-Martinez et al, (2014) "Versatile, High Quality and Scalable Continuous Flow Production of Metal-Organic Frameworks", Scientific Reports 4, Article number: 5443 doi: 10.1038/srep05443 ("Rubio-Martinez 2014"), the contents of which are to be understood to be incorporated into this specification by this reference.

Aluminium fumarate (Al-fum) and aluminium terephthalate (MIL-53) were used as each exhibit high thermal stability up to 450° C. and present a reversible uptake/release of water provided by an octahedral aluminium configuration and a strong Al—O bond. Both of these MOFs present very similar structures where the carboxylate groups of the corresponding linkers lead to the formation of a 3D structure with rhombohedral channels interconnected by infinite Al—OH—Al chains.

Figure 2A:
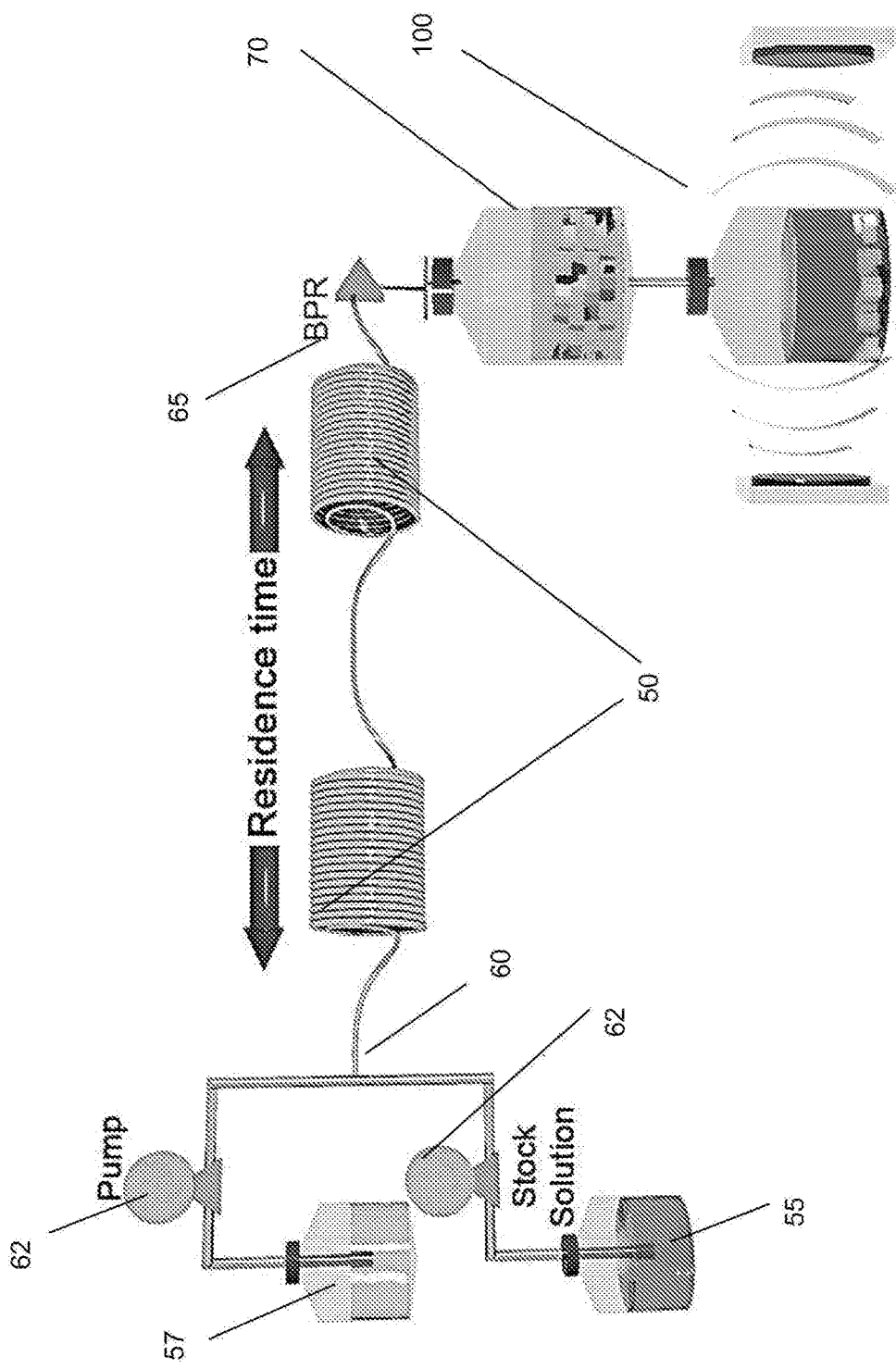
FIG. 2A provides a schematic representation showing the general flow reactor setup for the production of metal-organic framework solutions which are subsequently treated using the treatment apparatus according to the present invention.
Figure 2B:
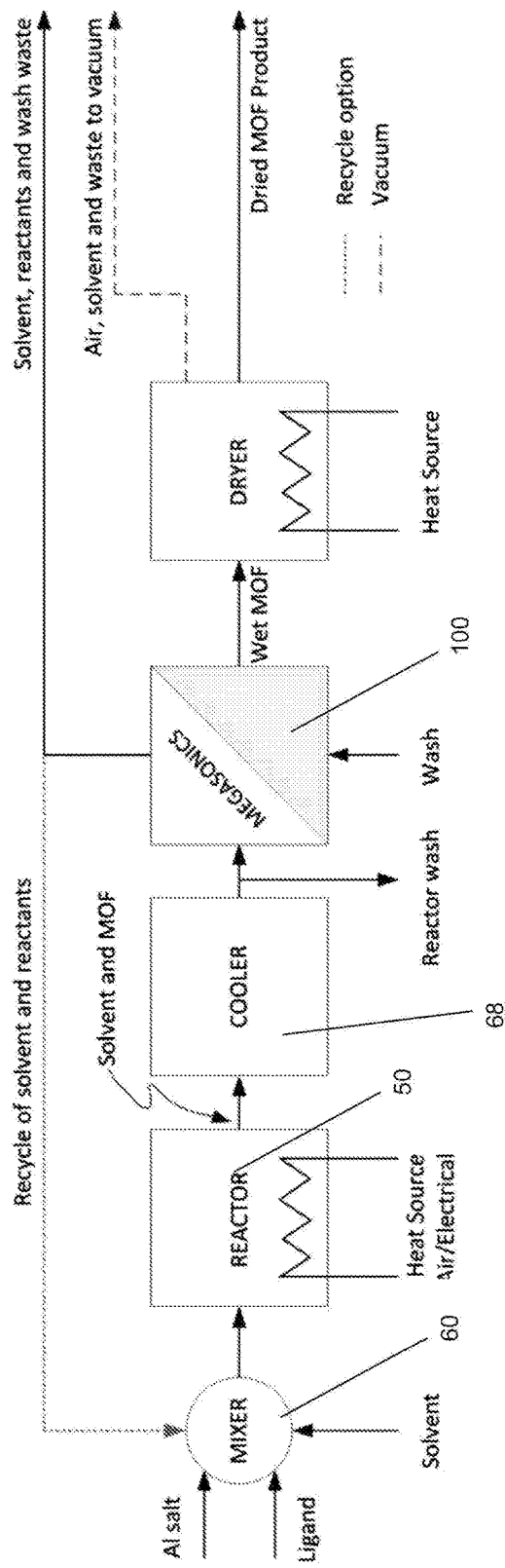
FIG. 2B provides a schematic representation showing the different stages of the continuous flow process for MOFs production: synthesis, washing, separation and drying.

A schematic representation showing the general flow reactor setup for the production of MOFs generally following Rubio-Martinez 2014 is shown in FIG. 2A. FIG. 2B shows another representative flow reactor configuration for MOF processing. Continuous flow scale-up synthesis was performed in a Salamander Flow Reactor (Cambridge Reactor Design Ltd., Cottenham, UK). Briefly, it consists of a reactor 50 comprising serpentine stainless steel tube (8 mm o.d., 6 mm i.d., 108 mL volume) and a thermostatically-controlled electrical heating system (ambient to 150° C.). An inline back-pressure regulator, situated at the outlet of the reactor, allows fine tuning of the reactor pressure (up to 20 bar). Static mixer units are placed within the linear sections of the reactor tubing to promote turbulent mixing and efficient heat transfer. Twin Gilson 305 dual piston pumps 62, (flow rates between 0.5 mL/min and 50 mL/min) provide the solvent and reagent feeds for the reactor system. Each separate precursor solutions of the organic ligand 55 and the metallic salt 57 are simultaneous pumped into a T-micro mixer 60 via pumps 62 using a commercially available flow chemistry synthesis platform. The mixed solvent streams are combined and directed into the coiled flow reactors 50. Each reactor coil 50 has its temperature regulated to be constant and homogenous throughout the reaction, eliminating the possible temperature gradients often observed in batch reactors. Preferably, the solvent, preferably water and/or mixture of water and ethanol, is kept at a temperature from about 25° C. to about 130° C. depending on the MOF synthesis. Typically, higher ligand concentration provides increased yields, however, the risk of blockage in the flow reactor 50 is also increased.

In a typical reaction, two separate solutions of the precursors are pumped through a T-type static mixer to promote diffusion mixing of the reagent input streams. The combined reagent streams are then directed into the heated reactor zone of the Salamander Flow Reactor for a predetermined residence time. On exiting the reactor, the MOF stream 65 is cooled in an external heat sink unit, based on a coiled tube in a water bath (FIG. 2B). Then the stream passes through a back-pressure regulator, and is collected for the next process steps. If desired, the solvent can be reused by recycling after the first separation stage. This is particularly attractive for recycling the unreacted ligand which is usually the most expensive reactant, or when an expensive or toxic solvent is used.

MOF stream 65 can be collected in a container or reservoir 70 which can then be subsequently fed into a megasonic separator 100 according to the present invention. This device is illustrated in more detail in FIG. 2C.

Synthesis of Al-Fumarate

The general procedure described above was employed. An aqueous solution of 0.35M $Al_2(SO4)_3$ $18H_2O$ and an aqueous solution of 0.7M of fumaric acid and 2M of NaOH solution were mixed under continuous flow conditions and heated in a tubular reactor. The synthesis was conducted at 65° C. using a total flow rate of 90 mL·$min^{-1}$, giving a total residence time of 1.2 min. The material was washed three times with fresh water and twice with ethanol and dried in vacuum (500 mbar) for 8 hours at 40° C. Yield: 100%.

S2.b. Synthesis of MIL-53 (Al)

The general procedure described above was employed. An aqueous solution of 0.08M $Al(NO_3)_3$ and an aqueous solution of 0.08M of terephthalic acid and 0.24M of NaOH solution were mixed under continuous flow conditions and heated in a tubular reactor. The synthesis was conducted at 140° C. using a total flow rate of 90 mL·min-1, giving a total residence time of 1.2 min. The material was washed three times with fresh water and twice with ethanol and dried in vacuum (500 mbar) for 8 hours at 40° C. Yield: 83%.

MOF Separation Process

The MOF crystals were isolated from the solvent using a megasonic apparatus and process according to one embodiment of the present invention. A conventional centrifuge was used as a control reference.

Figure 2C:
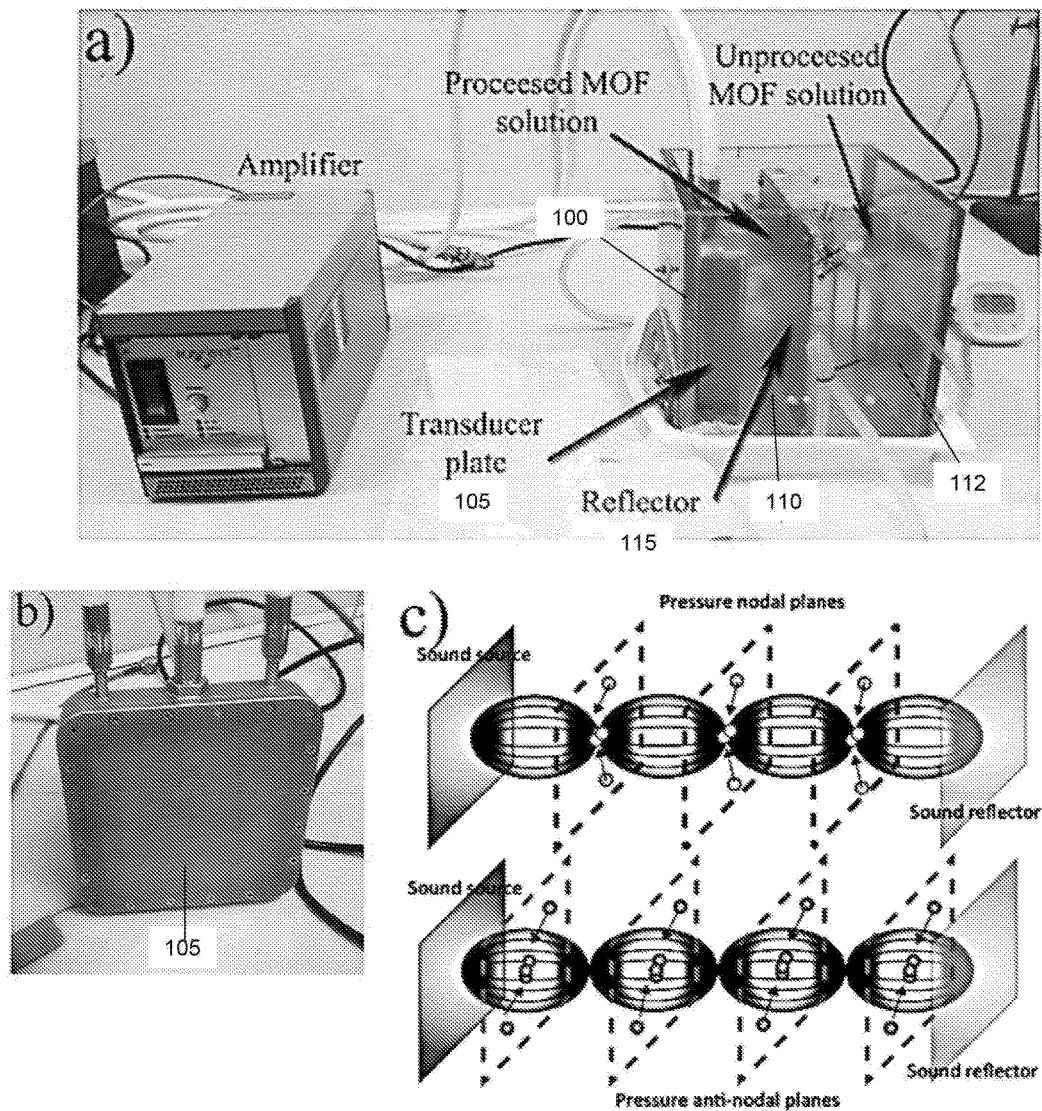
FIG. 2C provides a) a photograph of a first separator set-up with a high frequency system according to an embodiment of the present invention; b) a photograph of one 2000 kHz plate transducer used in the reactor set up shown in (a); and c) a schematic of a standing wave pattern formed by the superimposition of a reflected sound wave within the megasonic separator shown in (a).

The megasonic separator 100 is shown in FIG. 2C. The megasonic separator 100 applies high frequency ultrasound to create a standing wave, i.e. regions of minimal pressure (nodes) and maximal pressure (antinodes) within a separation chamber 110 of megasonic separator 100.

FIG. 2C(a) shows the megasonic separator 100 set-up with a high frequency system using one 2000 kHz plate transducer 105 (best shown in FIG. 2C(b)). All trials were conducted utilizing submersible stainless steel transducer plates (Sonosys Ultraschallsysteme GmbH, Neuenbuerg, Germany). The megasonic separator 100 essentially comprises a 1.1 L stainless steel container. It should be noted that a clear polycarbonate 6-liter container shown in the Figures was used initially to visualize the separation process. However, normal operation and experiments were performed in a 1.1-liter stainless steel container (not pictured).

The illustrated clear polycarbonate 6-liter container is split into two sections, a 1.1 L treatment section 110 containing the transducer plate 105 and an unprocessed section 112. The treatment section 110 and unprocessed section 112 are separated by a metallic (stainless steel) reflector plate 115 used to reflect the megasonic waves.

The plate transducer 105 was used for sonication at a frequency of 1 and 2 MHz (290 W) in separate trials for 10 min. Each experiment consisted of filling the acoustic reactor with a diluted MOF solution (50% in water) and immediately sonicating for 10 min. A control system, where no ultrasound was applied, was simultaneously filled with a portion of the same MOFs solution to observe the differences. In all experiments the temperature increased up to 10° C., caused by acoustic energy dissipation, therefore an ice bath is used during the experiments.

Before and after the application of ultrasound, 10 mL samples were removed to measure the ζ-potential of the MOFs. Using megasonics the MOF product was washed three times with fresh water and twice with EtOH.

FIG. 2C(c) shows the schematic of the standing wave pattern formed by the superimposition of a reflected sound wave within the treatment section 110. The separation distance between adjacent nodes or antinodes, is half a wavelength. Depending on the specific density and compressibility of the particles, they will collect either in the nodal (top, black dotted planes) as for the bright yellow particles or antinodal (bottom, red dotted planes) pressure planes as for the darker yellow particles. As previously noted, suspended particles or droplets migrate specifically towards one of these two regions due to acoustic radiation forces, based on their density and compressibility. In general, the aggregated MOFs are slightly denser than the surrounding fluid, and migrate towards the pressure nodes. As shown in FIG. 3, this gathering of MOF material enhances the tendency to form larger aggregates which then sediment settles at a greatly accelerated rate to the bottom of the separation chamber, where they can be collected.

Figure 3A:
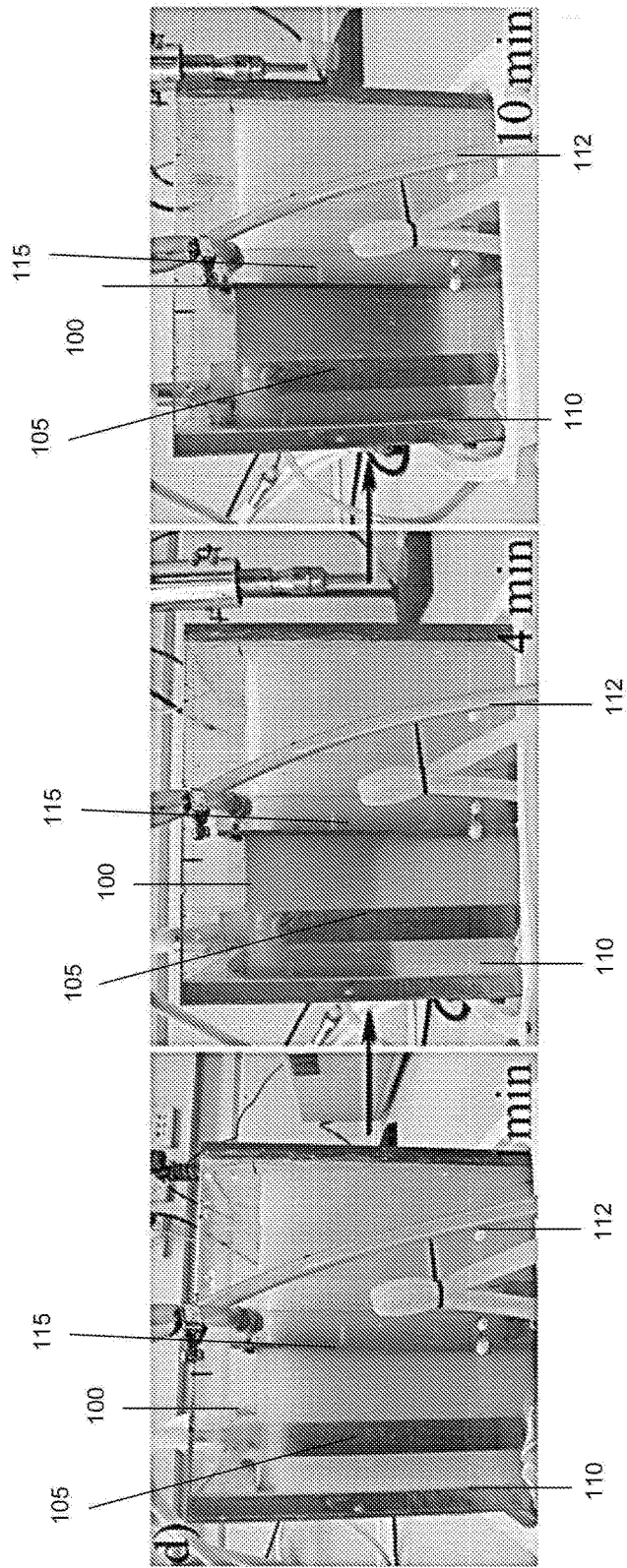
FIG. 3A provides three photographs of solution being treated in the separator shown in FIG. 2C at specific times (1 minute, 4 minutes and 10 minutes) during a process according to one embodiment of the present invention.
Figure 3B:
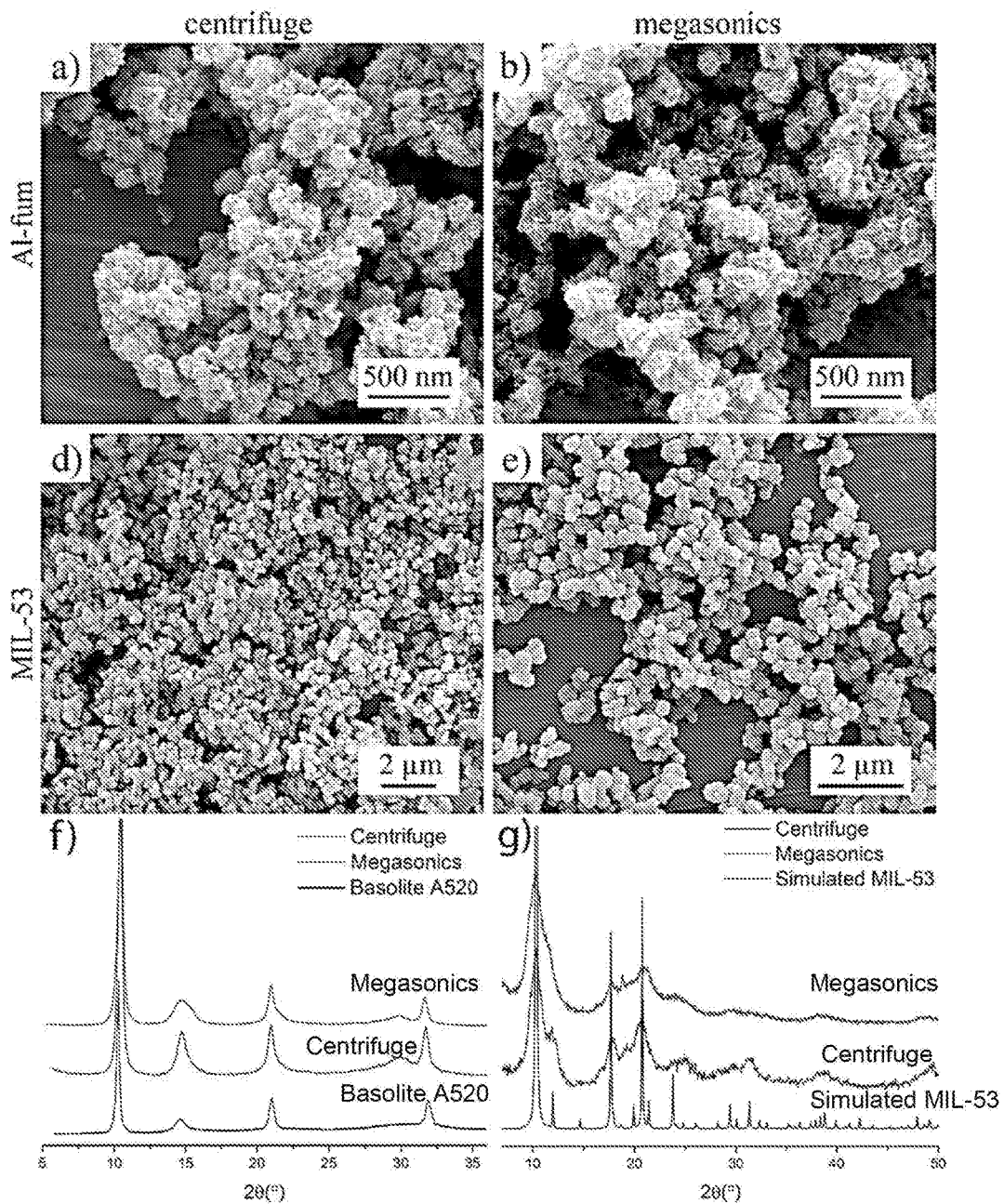
FIG. 3B provides a comparison of SEM images of (a) and (b) Al-fum, (d) and (e) MIL-53 using conventional centrifuge separation on the left and megasonics on the right; (f) and (g) Comparison of the XRD pattern diffraction of the megasonic and centrifuge product compared to a calculated pattern for Al-fum and MIL-53 respectively.
Figure 3C:
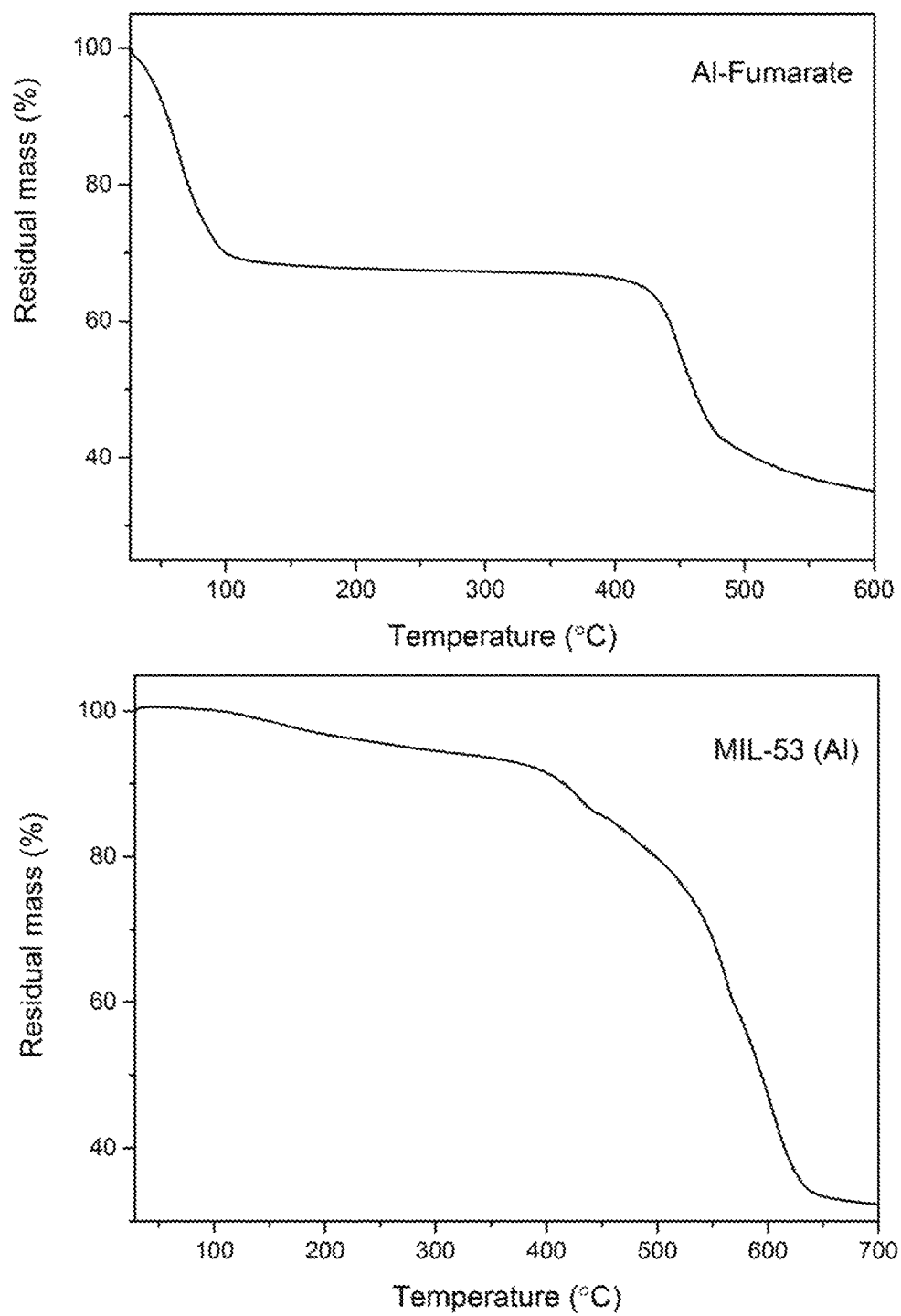
FIG. 3C provides a thermogravimetric analysis of Al-Fumarate and MIL-53 (Al) (heating rate: 5° C./min).

FIG. 3A provides three photographs of a MOF containing solution being treated in a megasonic treatment apparatus 100 shown in FIG. 2C(a) at specific times (1 minute, 4 minute and 10 minutes) during the megasonic separation process described above. In the left or separation compartment 110, the megasonic separation and purification process of the Al-MOF is shown. The right compartment 112 shows the same MOF containing solution without sonication. The settling of the MOF is clearly visible in the separation compartment 110 after 4 mins and 10 mins compared to the cloudiness of the same MOF containing solution without sonication shown in the right compartment 112.

The inventors believe that the precise mechanism may be related to changes in the local density that the aggregates experience due to varying size distribution of the nanosized MOF crystals. Generally, the influence of ultrasound on suspended particles depends on particle size, density and ultrasonic field. However, the resultant separation can be further influenced by possible interactions between MOF particles when they collide (i.e. surface properties). The solvent properties will also influence the specific density of the particles in the field, so that may also affect the separation efficiency as well. For the MOFs structures and solvent studied in these experiment, no appreciable differences were observed.

To determine the quality of the crystals, the MOFs separated with megasonic treatment apparatus 100 and a standard lab-scale centrifuge were compared by XRPD and SEM measurements. X-Ray powder diffraction (XRPD) confirmed the crystallinity of Al-fum and MIL-53, showing identical patterns to those of crystals synthesized by solvothermal methods. Note that the Megasonics separation had no impact on the crystallinity of the materials as demonstrated by identical pattern diffraction (See FIGS. 3B(f) and (g)). From the SEM images it was observed that the high-frequency treatment did not affect the size and shape distribution of the MOFs (See FIG. 3B). The thermo gravimetric analysis (TGA) curves showed a continuous weight loss over the temperatures ranges 50 to 100° C. due to water loss and thermal stability up to 450° C. (see FIG. 3C).

The scanning electron microscopy (SEM) images were collected on a Quanta 400 FEG ESEM (FEI) at acceleration voltage of 0.2-30 kV. Infrared (IR) spectra were recorded on a Tensor 27FTIR spectrophotometer (Bruker). The X-ray powder diffraction (XRPD) measurements were performed with an X'Pert Pro MPD diffractometer (Panalytical) over a 2θ range of 5° to 45°. The thermogravimetric analysis (TGA) was performed on a Perkin-Elmer STA-600 under a constant flow of $N_2$ at a temperature increase rate of 5° C./min. Zeta potential measurements were performed on a NanoZs Zetasizer from MALVERN whereas the Turbiscan measurements were performed with the MA 2000 (Formulaction, Toulouse, France). Gas adsorption isotherms for pressures in the range 0-120 kPa were measured by a volumetric approach using a Micrometrics ASAP 2420 instrument. All the samples were transferred to pre-dried and weighed analysis tubes and sealed with Transcal stoppers. Al-Fumarate and MIL-53 were evacuated and activated under dynamic vacuum at $10^{-6}$ Torr at 140° C. for 8 hours.

Ultra-high purity $N_2$, $CH_4$, $H_2$ and $CO_2$ gases were used for the experiments. $N_2$ and $H_2$ adsorption and desorption measurements were conducted at 77K. Surface area measurements were performed on $N_2$ isotherms at 77K using the Brunauer-Emmer-Teller (BET) model with adsorption values increasing range of 0.005 to 0.2 relative pressures while the $CH_4$ adsorption and $CO_2$ adsorption measurements were done at 273 and 298 K, respectively.

Example 2

Investigation into Changes in MOF Composition

In order to investigate whether megasonics separation introduces changes in the MOF composition, ζ-potential measurements were recorded after each washing step of Example 1 as shown Table 2.

TABLE 2

ζ-Potential of the Al-Fumarate and MIL-53 MOF material after each wash step using Megasonics using water as a dispersant.

| MOF washing process (Megasonics) | ζ-potential (mV) |
| --- | --- |
| Al-Fumarate flow reactor | +8.3 ± 0.4 |
| Al-Fumarate wash 1 in $H_2O$ | +8.8 ± 0.0 |
| Al-Fumarate wash 2 in $H_2O$ | +8.8 ± 0.1 |
| Al-Fumarate wash 3 in $H_2O$ | +8.9 ± 0.2 |
| Al-Fumarate wash 4 in EtOH | +10.6 ± 0.2 |
| Al-Fumarate wash 5 in EtOH | +11.3 ± 0.8 |
| MIL-53 flow reactor | +13.3 ± 0.4 |
| MIL-53 wash 1 in $H_2O$ | +15.1 ± 0.5 |
| MIL-53 wash 2 in $H_2O$ | +14.7 ± 0.3 |
| MIL-53 wash 3 in $H_2O$ | +12.6 ± 0.5 |
| MIL-53 wash 4 in EtOH | +12.7 ± 0.2 |
| MIL-53 wash 5 in EtOH | +14.6 ± 0.1 |

No significant changes to the surface charge were observed, pointing to a separation that is based on reversible aggregation.

To determine the quality of the crystals, XRPD and SEM measurements of the MOFs separated with megasonics and by the standard lab-scale centrifuge were compared. X-Ray powder diffraction (XRPD) confirmed the crystallinity of our Al-fum and MIL-53, showing identical patterns to those of crystals synthesized by solvothermal methods. It was observed by scanning electron microscope that the high-frequency treatment also does not affect the size and shape distribution of the MOFs.

A comparison of the backscattering and transmission data of the supernatant collected from the first separation of the MOF containing solution using centrifuge and megasonics was undertaken as shown in FIG. 4. As shown in FIG. 4, the recoverable MOF yield obtained with megasonic separation compared to the conventional centrifuge method is 3% less for each washing step. This difference can be attributed to the fact that centrifuge separation generates a higher G-force compared to the settling by gravity in megasonics, which leads to a more effective removal of the MOF material.

Figure 4A:
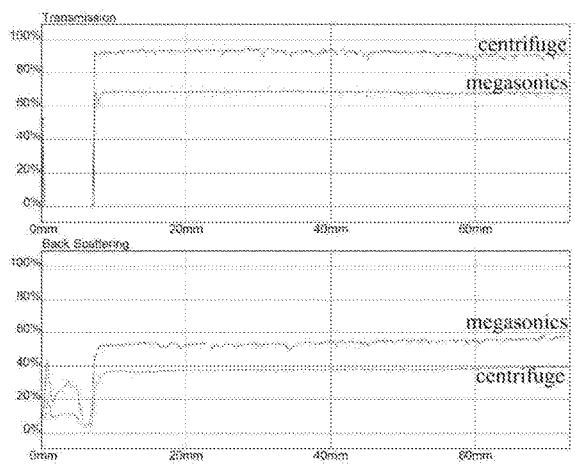
FIG. 4A provides a photographic comparison and a comparison plot of the backscattering and transmission data of the supernatant collected from the first separation of the MOF containing solution using centrifuge and applied frequencies (megasonic) for (A) Al-Fumarate supernatant; and (B) MIL-53 (Al) supernatant.
Figure 4A:
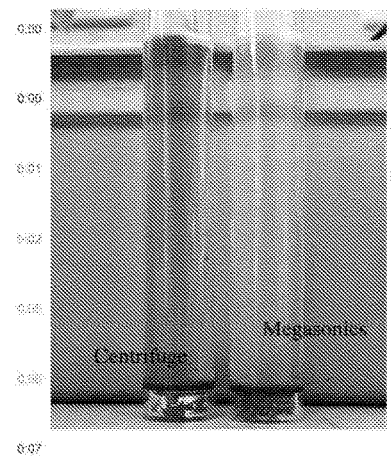
Figure 4A:
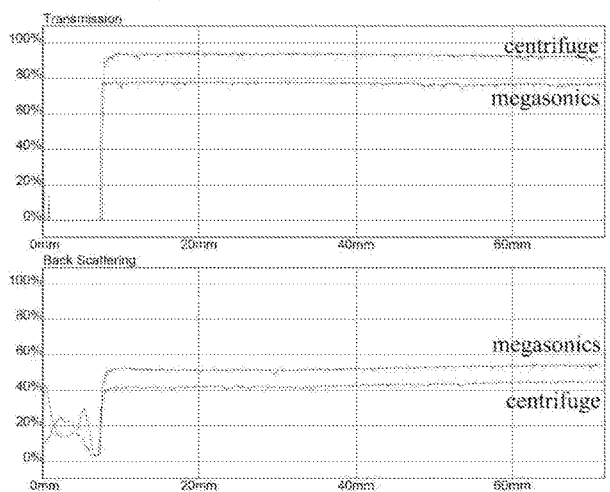
Figure 4A:
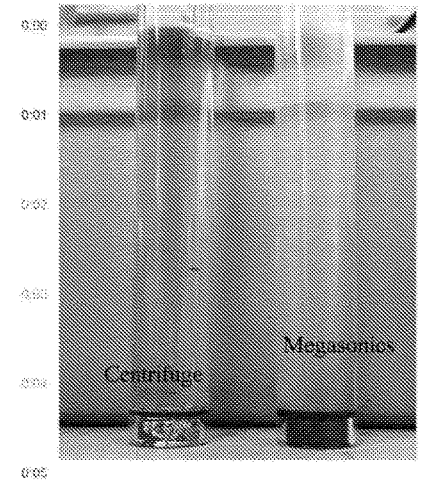
Figure 4B:
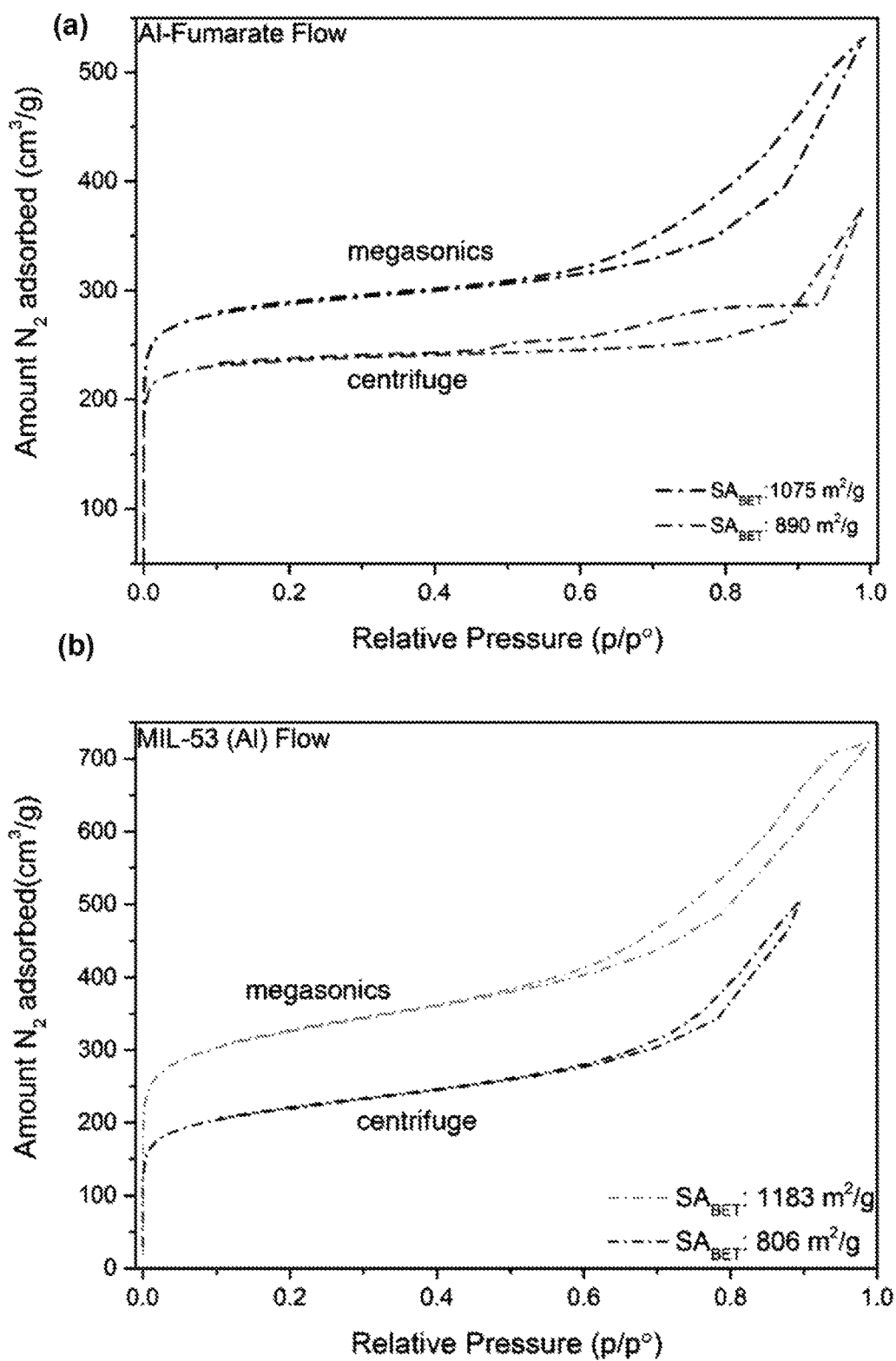
FIG. 4B provides representation of BET surface area, $SA_{BET}$ showing the difference between the product isolated with megasonic and centrifuge for (a) Al-fum; and (b) MIL-53, respectively.

The measurements of the BET surface areas revealed that the MOFs separated and washed with megasonics showed a drastic increase of 21% for the Al-Fum and 47% for MIL-53 over standard centrifuge washed MOF, which had BET values similar to literature (see Table 3 and FIG. 4B).

TABLE 3

Comparisons of the reaction time between MOFs synthesized by convectional batch (using water as a reaction solvent) and by flow chemistry. BET surface areas, grams of MOF produced per 1 hour using flow chemistry and STY. Full adsorption isotherms are provided in the supplement information.

| | Reaction time | g h$^{-1}$ | Yield (%) | STY (Kg·m$^{-3}$·d$^{-1}$) | SA$_{BET}$ (m$^2$ g$^{-1}$) |
|---|---|---|---|---|---|
| From reactor | | | | | |
| Al-fum | 1.2 min | 338.04 | 109.0 | 25,040 | — |
| MIL-53 | 1.2 min | 50.68 | 112.8 | 3,754 | — |
| Centrifuge × 5 | | | | | |
| Al-fum | 1.2 min | 281.88 | 90.9 | 20,880 | 890 |
| MIL-53 | 1.2 min | 42.14 | 93.8 | 3,121 | 806 |
| Megasonics × 5 | | | | | |
| Al-fum | 1.2 min | 225.07 | 72.6 | 16,672 | 1075 |
| MIL-53 | 1.2 min | 35.10 | 78.1 | 2,600 | 1183 |
| Commercial[a] Al-fum | 10.2 min | 174 | 86 | 5339 | 1140 |
| Literature[b] MIL-53 | 4 hours | 125 | 86 | 1300 | 1010 |

[a] M. Gaab, N. Trukhan, S. Maurer, R. Gummaraju and U. Müller, *Microporous Mesoporous Mater.*, 2012, 157, 131-136.
[b] P. A. Bayliss, I. A. Ibarra, E. Pérez, S. Yang, C. C. Tang, M. Poliakoff and M. Schröder, *Green Chem.*, 2014, 16, 3796.

The Inventors attribute this improvement to the enhanced mass transfer that arises from acoustic streaming during megasonic application that promotes the removal of the excess organic ligands molecules inside of the pores. This is an important step forward for cost-effective and green production of MOFs as similar surface areas have only been obtained using laboratory scale methods that would be expensive at large scale, namely by using supercritical ethanol or calcination up to 330° C.

Example 3

MOF Characterisation and Separation Parameters

Megasonics Characterisation

Figure 5:
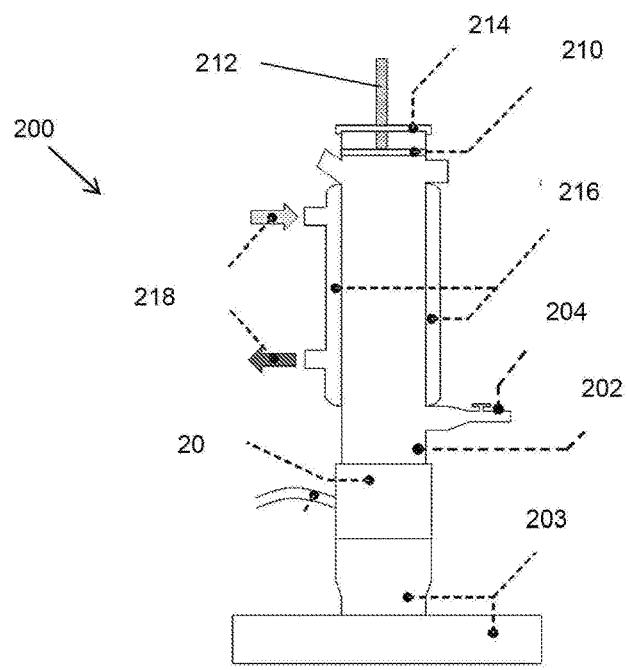
FIGS. 5 and 6 shown the experimental set up of a second separator set-up with a high frequency system according to an embodiment of the present invention.
Figure 6:
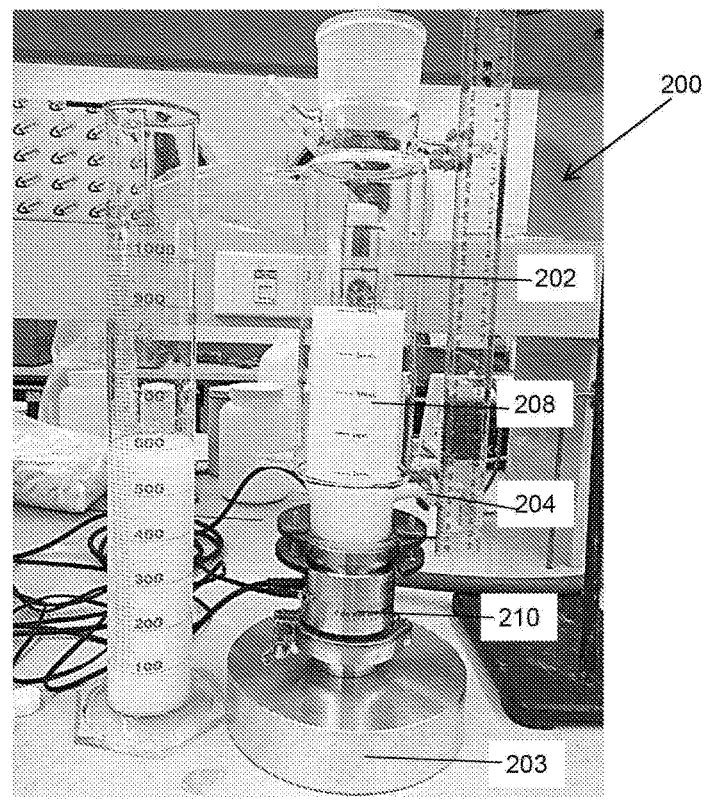

The separation of the MOFs was carried out in the experimental set up 200 shown in FIGS. 5 and 6. This separation arrangement comprised an open-ended cylindrical glass vessel 202 with a capacity of 1 L mounted on a stand or base 203. A glass valve (sampling valve 204) was attached to the lower vessel opening to allow easy sampling of the solids bed, post separation. A piezoelectric transducer 205 (E 805/T/M Meindhardt Ultrasound Transducer) was positioned at the base of the cylinder, which made a water tight seal with the vessel 202. The transducer 205 was capable of operating are three separate frequencies (578, 860, 1138 kHz) in either pulse or continuous configurations. However only continuous was used for the experiments. Ultrasonic signals were generated using an ultrasonic multi-frequency generator (Meindhardt, not illustrated) and power output could be adjusted to a nominal value between 0 and 100%. The vessel 202 was filled with various volumes of MOF (208-FIG. 6) and a stainless steel reflector 210 (thickness 0.5 cm) was positioned to be in contact with the slurry. The reflector 210 was connected to a steel threaded rod 212 which could move freely through a lid 214, allowing the height of the reflector 210 to be altered. The system also included a cooling jacket 216 which where necessary used a flow of cooling water 218 to cool the mixture contained in the vessel 202.

The power draw of the system 200 was determined using a standard power meter (not illustrated), although obtaining an accurate reading was difficult given the large fluctuations at each frequency. The average power draw of the system 200 at each frequency was determined over a 10 minute period of operation with a measurement taken at each minute interval from the power meter. At the completion of the 10 minute period the average power draw of the system at each frequency was determined. At frequencies of 1138, 860 and 578 kHz the power draw of the system was found to be 399±7, 422±2 and 408±17 W, with the baseline power draw (whilst no ultrasonics were generated) of 84 W. This suggests the transducer's 210 power output for each of the frequencies (1138, 860 and 578 kHz) were 315±7, 338±2 and 324±17 W.

Separation Optimisation

Several parameters were of interest when attempting to optimise the separation of the MOF; these included frequency, and reflector height.

In order to determine the best frequency for MOF separation the megasonics vessel was first filled with 500 mL of clean (pre washed) Al-Fum and a frequency (1138, 860 or 578 kHz) was selected. Megasonics were then applied for a period of 10 minutes at 100% power and a reflector height of 14.5 cm, for the chosen frequency. At the end of the treatment period, the megasonics were switched off and the slurry allowed to freely settle for a period of 15 minutes. Following separation, the supernatant was decanted using a peristaltic pump and the volume was recorded before two solids samples were taken using the solids sampling valve 204 (FIG. 5). The mass of each of the solids samples was weighed before being dried overnight. The solids fraction (mass of solids per mass of slurry) was determined for each sample in order to characterise the degree of separation achieved. Finally, the process was repeated for the remaining two frequencies. The experiment was then repeated for each frequency without the use of a reflector.

Again the same Al-Fum MOF was left overnight before tests were undertaken to investigate the effect of reflector height. The vessel was filled to heights of 11.5, 14.5, 20.5 and 26.5 cm in succession, with megasonic treatment of 10 minutes at 100% and 1138 kHz. The MOF was once again allowed to settle for a period of 15 minutes before supernatant volume and bed mass fractions were taken in the same way as earlier described.

Activation of MOF

Following separation optimisation, transition was made from clean pre-washed MOF to reactor slurry in order to characterise the effects of the megasonics on both the activation process as well as any changes to the MOFs structure. In order to achieve this, 500 mL of Al-Fum reactor slurry was diluted to a 3 L batch. From this batch 500 mL was added to the megasonics vessel 202 and sonicated for 10 minutes at 100% power output with a frequency of 1138 kHz. At the conclusion of the treatment, the slurry was allowed to freely settle for 15 minutes before a solids sample was taken (8 mL) from the top layer (1 cm) of the bed. A peristaltic pump was then used to remove a total of 100 mL of supernatant. 100 mL of fresh water (milliQ grade) was added to the vessel prior to removal of the slurry from the megasonics vessel 202. The slurry was stirred briefly and a small sample (<5 mL) was taken for SEM analysis before being re-added to the vessel 202 for a further treatment. This was repeated until a total of 4 cycles (washes) had been completed. At the conclusion of the final washing stage, additional solids were removed for BET analysis.

As a comparison, 500 mL of the same batch of diluted Al-Fum was centrifuged at 4500 RPM for 5 minutes. A small solids sample was taken for XRD analysis prior to the removal of 100 mL of supernatant. This was replaced with 100 mL of fresh water; the separated MOF was agitated before the process was repeated for a total of 4 washes. At the completion of 4 washes, additional solids were removed for the purpose of BET analysis.

Post reactor Mil-53 slurry was then used in place of Al-Fum and the same tests were repeated although in this case separation was achieved without initial the dilution (500 mL to 3 L) given its already dilute nature.

Results and Discussion

Figure 7:
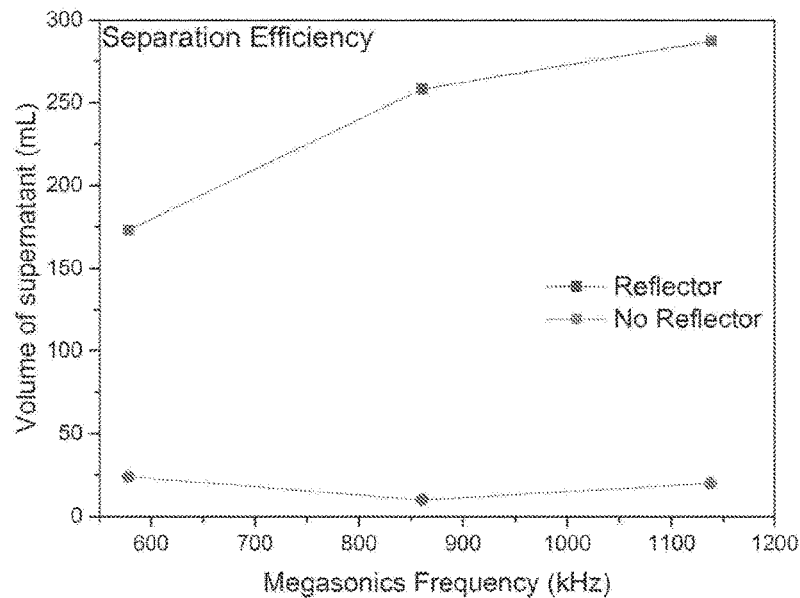
FIG. 7 provides a plot of obtained supernatant volumes following megasonic separation of Al-Fum MOF for various frequencies. The total volume of MOF containing solution is 500 mL FIG. 8 provides a plot of the mass faction vs reflector distance or spacing from the transducer.

Optimal Frequency—Carrying out treatments at each frequency, the greatest MOF separation (and hence greatest amount of separation) was achieved when treatment occurred with a frequency of 1138 kHz rather than 860 or 578 kHz (FIG. 7). This is supported by the obtained mass fractions within the bed which show the highest concentration of MOF present within the bed when 1138 kHz are used. On the other hand, the same experiments performed without the reflector did not achieve separation, which indicates that in order to isolate the MOF the formation of standing waves is required. The standing wave generates regions of minimal pressure (nodes) and maximal pressure (antinodes) within a separation chamber. Due to local acoustic radiation forces, suspended MOF particles migrated specifically towards the regions of minimal pressure (nodes) and maximal pressure (antinodes). This gathering of MOF material enhanced the tendency to form larger aggregates, which then settle at a greatly accelerated rate to the bottom of the separation chamber, where they were collected.

Figure 8:
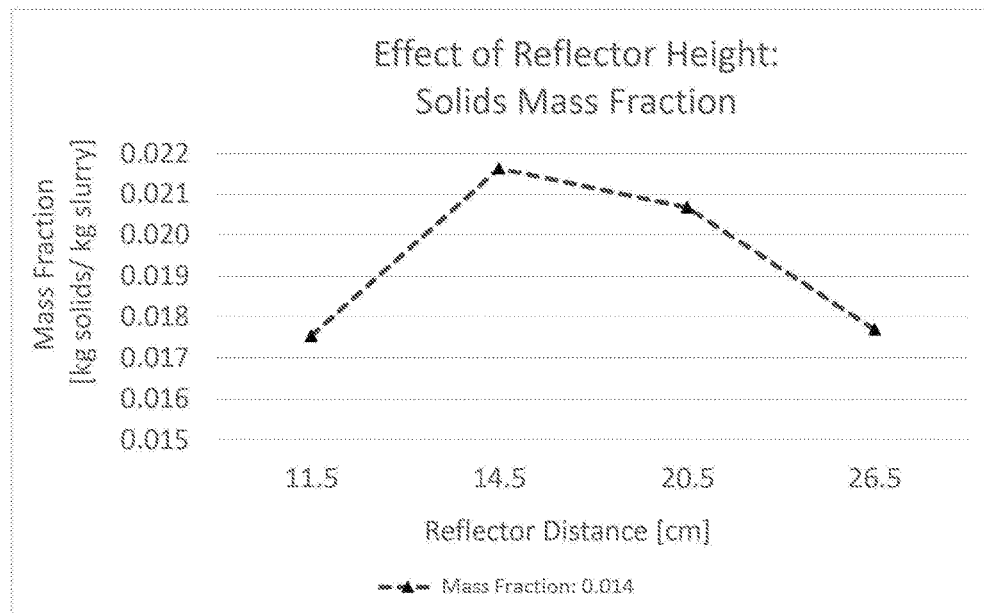
Figure 9:
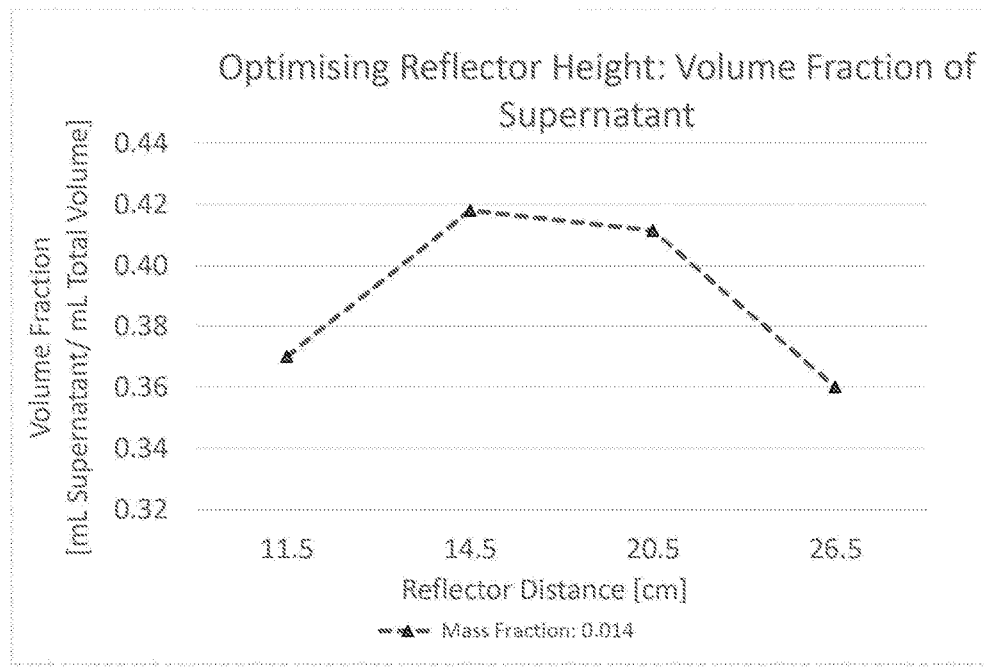
FIG. 9 provides a plot of volume fraction vs reflector distance or spacing from the transducer.

Effect of Reflector Height—Various reflector heights (11.5, 14.5, 20.5 and 26.5 cm) were analysed for their effect on the degree of separation. Tests were carried out in this case at a frequency of 1138 kHz given that is was expected to be the most highly attenuating (lowest operable distance, Section 2.1.3) and was observed to give the highest degree of separation. From FIGS. 8 and 9, it appears that the greatest degree of separation occurs at a mid-range reflector height of approximately 14.5 cm. At lower heights (11.5 cm) lower bed mass fractions were observed as well as lower volume fractions (volume of supernatant per total volume). This could be potentially due to increased streaming given the lower volume of slurry present which would in turn reduce the degree of separation (as outlined above).

At greater reflector heights (20.5 cm and 26.5 cm), it was found that once again separation was reduced when compared to separation when using a reflector at 14.5 cm. This is undoubtedly due to acoustic attenuation which sees the amplitude of the sound die out at longer treatment distances. Although 14.5 cm was identified as the optimal reflector height, it did not lead to significant increases in the degree of separation and successful separations were carried out all heights (11.5 cm-26.5 cm).

Activation of Metal-Organic Frameworks—Comparing the effects of megasonic activation to centrifugation (Table 4), it is clear that significantly higher surface area has been achieved when megasonic treatment is applied. The measurements of the BET surface areas revealed that the MOFs separated and activated with megasonics showed an increase of 25% after 10 minutes (for the Al-Fum over standard centrifuge washed MOF, which had BET values similar to literature). We attribute this improvement to the enhanced mass transfer that arose from acoustic streaming during megasonic application promoting the removal of excess organic ligands molecules from the pores of the MOF crystals.

TABLE 4

Water washing comparison, BET isotherms for centrifuge and megasonic Al-Fum washes at different times at 1138 kHz

| Methods | $SA_{BET}$ (m$^2$/g) |
|---|---|
| Centrifuge | 880 |
| Megasonics 1 min | 907 |
| Megasonics 5 min | 916 |
| Megasonics 10 min | 975 |
| Megasonics 10 min in ETOH | 1075 |

Example 4

Continuous Megasonics Operation

Figure 10:
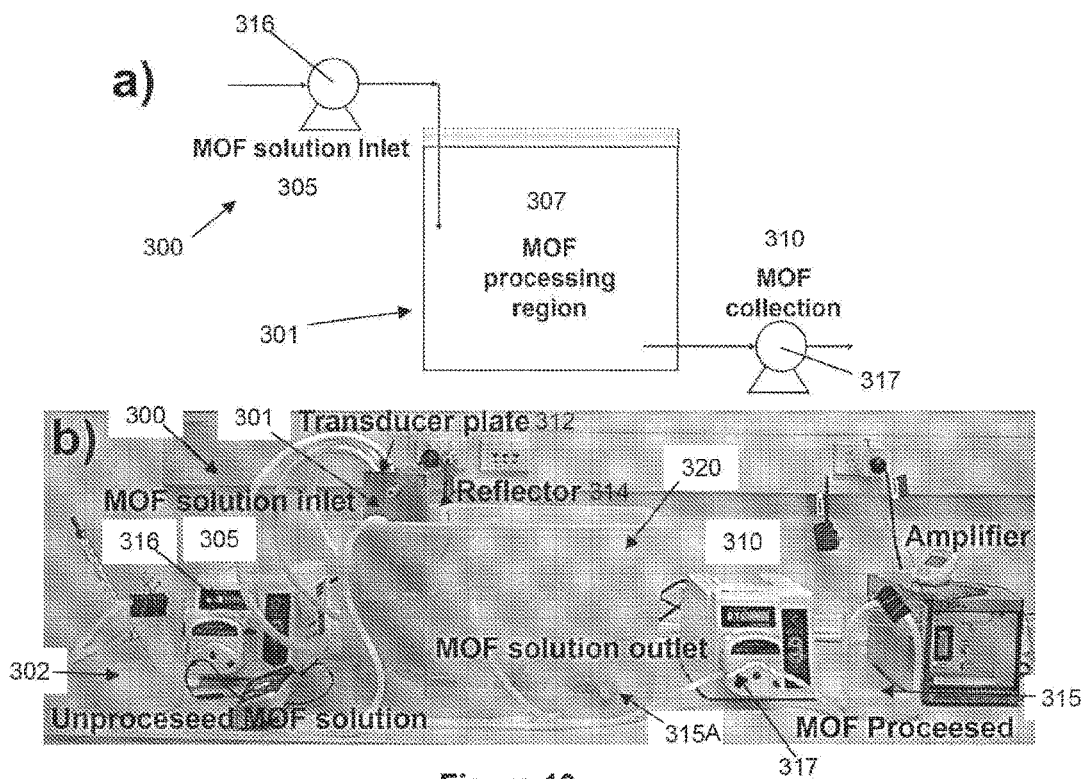
FIG. 10 provides a) Schematic of inlet and outlet flows into prototype MOF separation and activation vessel. b) The ultrasonic continuous reactor set-up with a high frequency system using one 1 MHz plate transducer.

A prototype Continuous MOF separation process arrangement 300 according to the present invention was trialled as illustrated in FIG. 10. In this regard, FIG. 10 provides a) schematic of inlet 305 and outlet flows 310 into prototype MOF separation and activation vessel 301 which encloses a MOF processing region 307 and b) a photograph of prototype MOF separation and activation vessel 301 including an ultrasonic continuous reactor set-up with a high frequency system using one 1 MHz plate transducer 312. As shown in both FIGS. 10(a) and 10(b), the process arrangement 300 comprises a solution inlet 305 which includes a fluid pump 316 to pump unprocessed MOF containing solution from feed flask 302 into the prototype MOF separation and activation vessel 301 which includes a MOF processing region 307 containing a fluid reservoir, a transducer plate 312 for applying the requisite frequency pulses into a selected region of the MOF processing region 307, a reflector plate 314 to reflect the original transmitted wave from the transducer plate 312 and form standing wave through constructive interference, a MOF containing solution outlet 310, which like the inlet includes a fluid pump 317 to pump processed MOF containing solution into a collection flask 315. The MOF separation and activation vessel 301 is held in an ice bath 320, as best shown in FIG. 10(b).

In the process trial, a MOF containing solution with an initial temperature of 15° C. fed from feed flask 302 into the processing region 307 of the vessel 301. The transducer plate 312 was then operated to initially pre-sonicate the MOF containing solution for 10 min (100% nominal power with the 1 MHz transducer) prior to beginning flow operation, resulting in an increased temperature of the MOF containing solution of 20-25° C. After this pre-sonication step, flow was initiated by turning on the pumps 316, 317 and opening a drain valve 315A located at the bottom of the vessel 301. The input of MOF containing solution, along with an ice cooling bath 320 located on the sides of the processing region 307, enabled temperature to be maintained within an optimal range for efficient MOF separation and activation of between 20 and 40° C. across the entire process duration. The processed MOF was collected by removing the solution from the drain valve 315.

Those skilled in the art will appreciate that the invention described herein is susceptible to variations and modifications other than those specifically described. It is understood that the invention includes all such variations and modifications which fall within the spirit and scope of the present invention.

Where the terms "comprise", "comprises", "comprised" or "comprising" are used in this specification (including the claims) they are to be interpreted as specifying the presence of the stated features, integers, steps or components, but not precluding the presence of one or more other feature, integer, step, component or group thereof.

The invention claimed is:

1. A method of separating a metal organic framework (MOF) from a solution, comprising:
    providing a MOF containing solution which includes a MOF;
    contacting the MOF containing solution with an acoustic reflector surface such that, any high frequency ultrasound applied within the MOF containing solution reflects off the acoustic reflector surface such that a standing wave is formed through constructive interference; and
    applying a high frequency ultrasound of at least 20 kHz to the MOF containing solution,
    thereby separating the MOF from solution as an aggregated sediment which settles out of solution.

2. The method according to claim 1, wherein the applied high frequency ultrasound is 20 kHz to 4 MHz.

3. The method according to claim 1, wherein the applied high frequency ultrasound is moved between a high frequency and a low frequency.

4. The method according to claim 3, wherein the high frequency is 400 kHz to 10 MHz and the low frequency is 20 kHz to 400 kHz.

5. The method according to claim 1, wherein the energy density of the applied high frequency ultrasound is at least 25 kJ/kg.

6. The method according to claim 1, wherein at least one of frequency or energy density of the applied high frequency ultrasound is tuned to selectively separate MOF and any contaminants in the MOF containing solution based on a specific particle size.

7. The method according to claim 1, wherein a metal organic framework (MOF) in the MOF containing solution includes at least one contaminant, and the method separates the MOF from the contaminant, the contaminant remaining in solution.

8. The method according to claim 1, wherein the step of providing the MOF containing solution comprises adding a MOF to a washing solution.

9. The method according to claim 8, wherein the washing solution comprises water, ethanol, dimethylformamide (DMF), methanol, tetrahydrofuran, chloroform, dichloromethane, ethyl acetate, diethylformamide or a combination thereof.

10. The method according to claim 7, wherein the at least one contaminant includes occluded unreacted ligands or metal salts within pores of the MOF.

11. The method according to claim 1, wherein the MOF containing solution comprises a mother liquid from a MOF forming process.

12. The method according to claim 1, wherein the method also improves the BET surface area of the MOF.

13. The method according to claim 1, further comprising: isolating the MOF.

14. The method according to claim 1, further comprising at least one washing step including the steps of:
    isolating the MOF;
    adding the isolated MOF to a washing solution;
    contacting the MOF containing washing solution with an acoustic reflector surface such that, any high frequency ultrasound applied within the washing solution reflects off the acoustic reflector surface such that a standing wave is formed through constructive interference; and
    applying a high frequency ultrasound of at least 20 kHz to a MOF containing solution, thereby separating any contaminant from the MOF within the solution.

* * * * *